(12) United States Patent
Cedarbaum

(10) Patent No.: US 6,656,474 B1
(45) Date of Patent: Dec. 2, 2003

(54) METHODS OF USING A NEUROTROPHIN AND ITS ANALOGUES FOR THE TREATMENT OF GASTROINTESTINAL HYPOMOTILITY DISORDERS

(75) Inventor: Jesse M. Cedarbaum, Larchmont, NY (US)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 0 days.

(21) Appl. No.: 09/232,171

(22) Filed: Jan. 15, 1999

(51) Int. Cl.[7] .......................... A61K 39/00; A61K 38/00
(52) U.S. Cl. ...................................... 424/198.1; 514/21
(58) Field of Search .......................... 424/185.1, 198.1, 424/200.1; 514/892, 12, 21, 867; 530/350, 839; 435/252.3, 252.33; 930/120; 935/13

(56) References Cited

U.S. PATENT DOCUMENTS

| | | | |
|---|---|---|---|
| 4,987,136 A | * 1/1991 | Kreek et al. | 514/282 |
| 5,571,675 A | * 11/1996 | Baker et al. | 435/6 |
| 5,616,724 A | * 4/1997 | Hudkins et al. | 548/417 |
| 5,723,585 A | 3/1998 | Baker et al. | 530/413 |
| 5,753,225 A | 5/1998 | Clary et al. | 424/130.1 |
| 5,759,775 A | * 6/1998 | Caras et al. | 435/6 |
| 5,770,577 A | * 6/1998 | Kinstler et al. | 514/21 |
| 5,798,448 A | 8/1998 | Caras et al. | 530/387.1 |
| 5,955,420 A | 9/1999 | Chen et al. | 514/2 |
| 5,962,404 A | * 10/1999 | Eisenbach-Schwartz | 514/2 |
| 6,174,701 B1 | * 1/2001 | Rosenthal et al. | 435/69.1 |
| 6,284,540 B1 | * 9/2001 | Milbrandt et al. | 435/455 |

FOREIGN PATENT DOCUMENTS

| | | |
|---|---|---|
| WO | WO 98/49308 | 11/1998 |

OTHER PUBLICATIONS (abstract) Chandra et al., Isolated thyrotrophin deficiency in diabetes mellitus.*
(abstract) Fiorani et al., [Hypothyroidism and megacolon].*
(abstract) Longo et al., "Teh colon, anorectum, and spinal cord patient. A review of the functional alterations of the denervated hindgut".*
(abstract) Gurnari et al., "Chronic Constipation After Gynecologiacal Surgery a Retrospective Study".*
(abstract) Berstock, "Hemorrhoidectomy Without Tears".*
(abstract) Tittle et al, "Pain and pain–related side effects in an ICU and on a surgical unit: nurses management".*
(abstract) Turpin et al., [Complications of antitumor and antileukemic chemotherapy. 1].*
Tessarollo et al., Targeted deletion of all isoforms of the trkC gene suggests the use of alternate receptors by its ligand . . . Proc. Natl. Acad. Sci. USA, vol. 94, pp. 14776–14781, 1997.*

Brunton, 1990, "Agents Affecting Gastrointestinal Water Flux and Motility, Digestants, and Bile Acids," *IN: Pharmacological Basis of Therapeutics, Eighth Edition*, Gilman et al. (eds.), pp. 914–932, Pergamon Press, New York.

Camilleri, 1998, "Gastrointestinal Motility Disorders," *In: Scientific American Medicine*, Dale and Federman (eds.), Scientific American, Inc., New York.

*Drug Evaluations, 6th Edition*, 1986, American Medical Association, Chicago, pp. 937–957.

Helke CJ et al., "Axonal transport of neurotrophins by visceral afferent and efferent neurons of the vagus nerve of the rat", J Comp Neurol. Mar. 30, 1998;393(1):102–117.

Nightingale, 1998, "From the Food and Drug Administration: New Warnings Added to Cisapride Labeling", JAMA. 280(5):410.

Schade RR et al., "Effect of metoclopramide on gastric liquid emptying in patients with diabetic gastroparesis", Dig Dis Sci. Jan. 1985;30(1):10–15.

Sleisenger et al., 1989, *Gastrointestinal Disease*, 4th Edition, HBJ, Inc., Philadelphia, pp. 675–713.

Hefti, 1994, Neurotrophic factor therapy for nervous system degenerative diseases, J. Neurobiol 25(11):1418–1435 (Abstract only).

Szarka et al., "Recombinant human neurotrophin–3 accelerates small bowel and colonic transit in healthy humans and patients with constipation", Gastroenterology 116(4):A1089. (Apr. 1999).

Yuen et al., 1996, "Therapeutic potential of neurotrophic factors for neurological disorders", Annals of Neurology 40(3):346–354.

Tomlinson et al., 1996, "Neurotrophins and Peripheral Neuropathy", Philosophical Transactions. Royal Society of London. Biological Sciences 351(1338):455–462.

Connor et al., 1998, "Growth Factor Therapy", Mental Retardation and Developmental Disabilities Research Reviews 4(3):212–222.

Chaudhry et al., 2000, "Tolerability of recombinant–methionyl human neurotrophin–3 (r–metHuNT–3) in healthy subjects", Muscle & Nerve 23(2):189–192.

Coulie et al., 2000, "Recombinant human neurotrophic factors accelerate colonic transit and relieve constipation in humans", Gastroenterology 119(1):41–50.

* cited by examiner

Primary Examiner—Marjorie Moran
(74) Attorney, Agent, or Firm—Pennie & Edmonds LLP

(57) ABSTRACT

The present invention relates to methods for enhancing gastrointestinal motility. In particular, the invention relates to the use of neurotrophin-3 and its analogues for enhancing gastrointestinal motility. Methods of using neurotrophin-3 and its analogues for treating gastrointestinal hypomotility disorders are also provided.

28 Claims, 17 Drawing Sheets

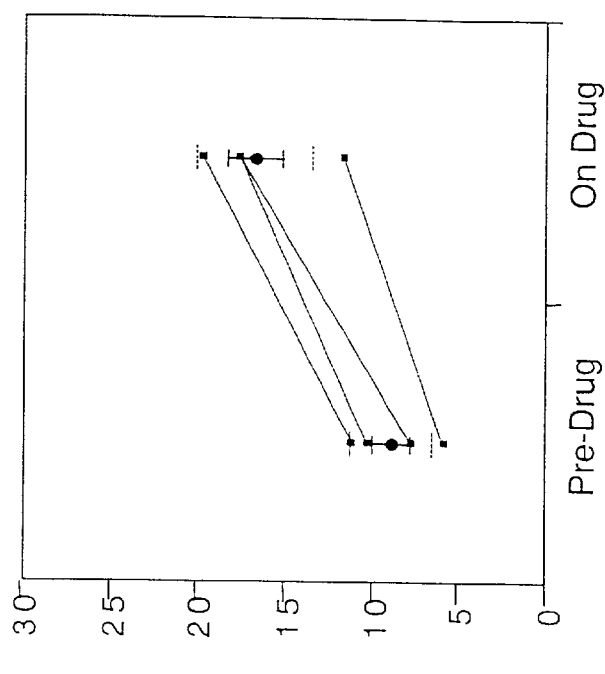
FIG. 2B Normal Volunteers
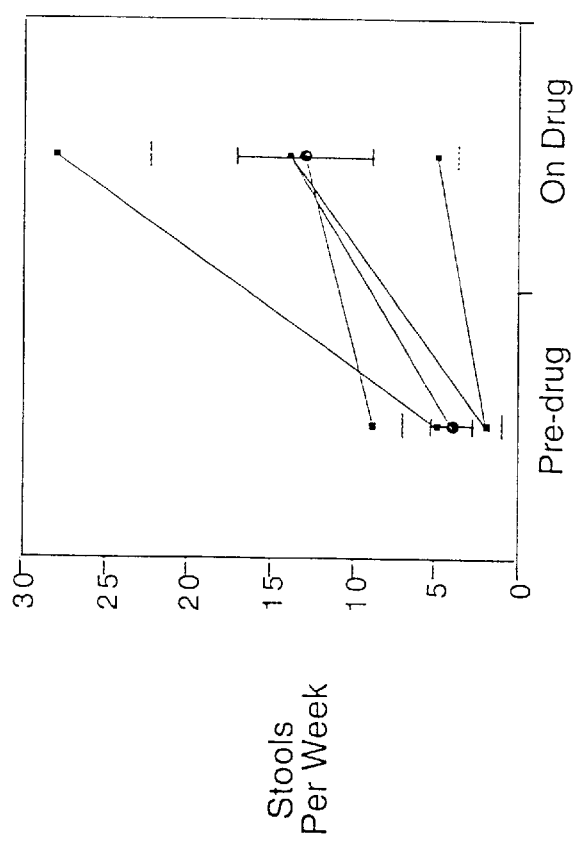
FIG. 2A Constipated Patients

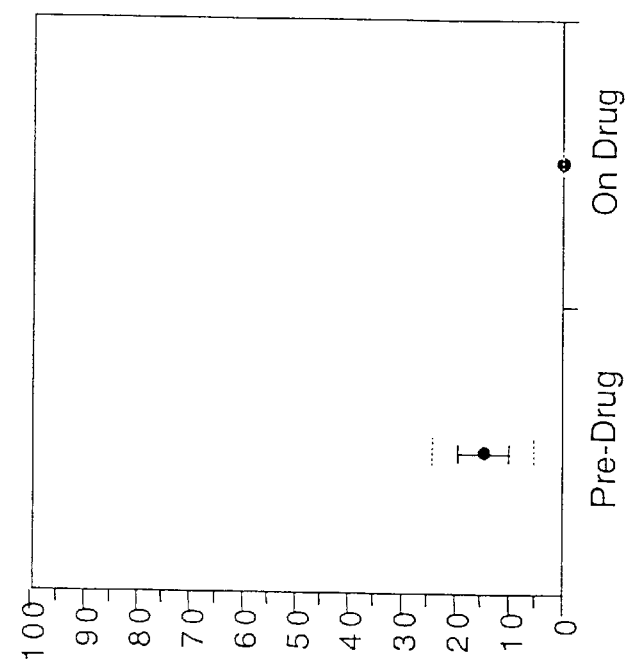
FIG. 3B Normal Volunteers
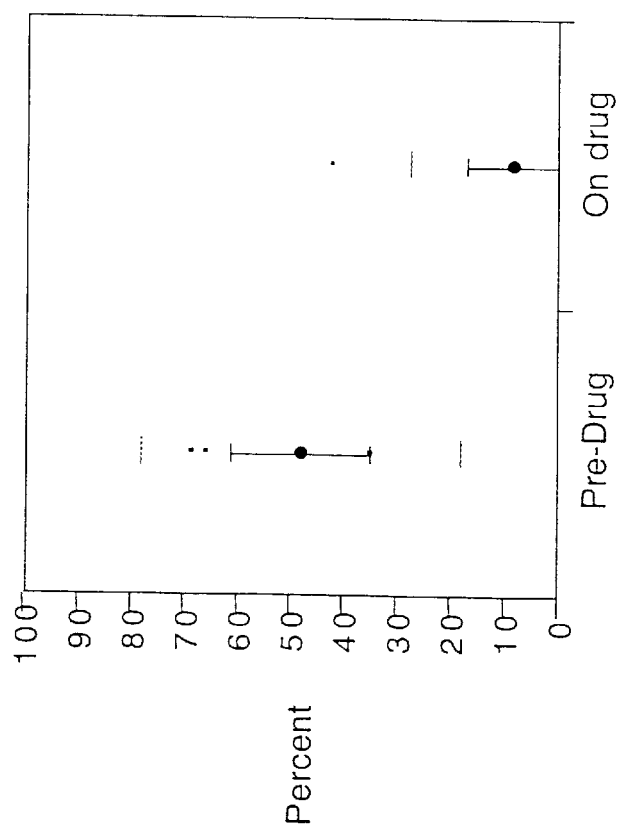
FIG. 3A Constipated Patients

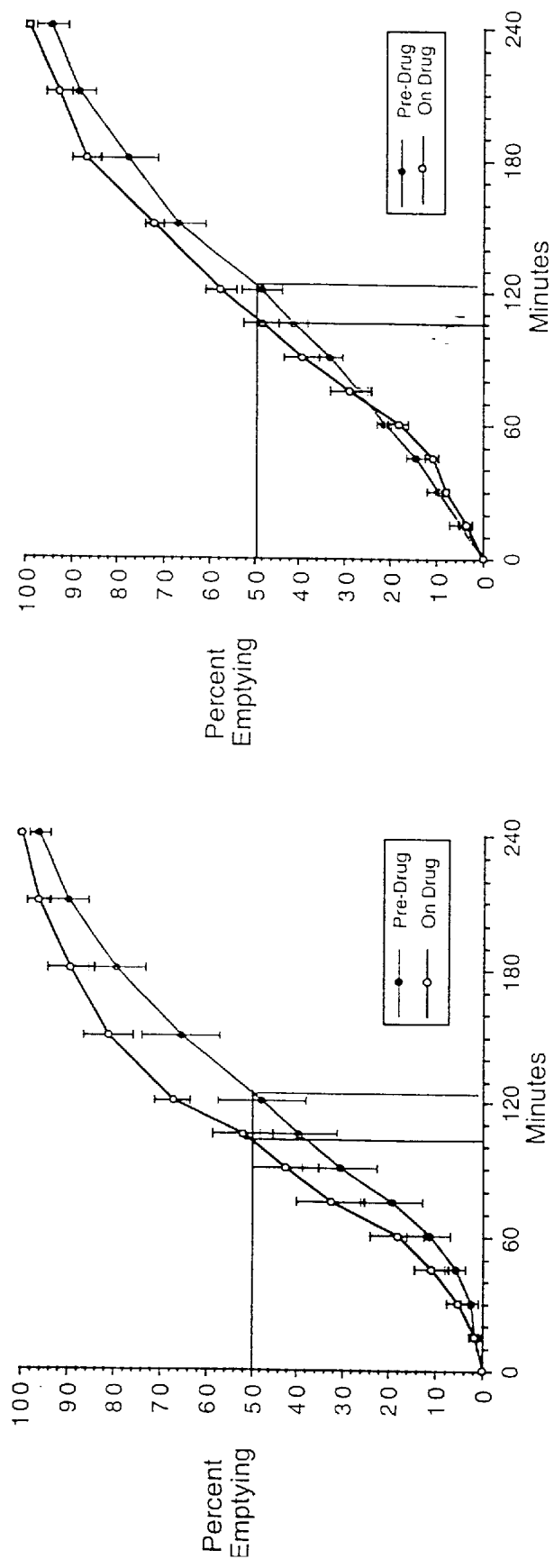
FIG. 5B Normal Volunteers
FIG. 5A Constipated Patients

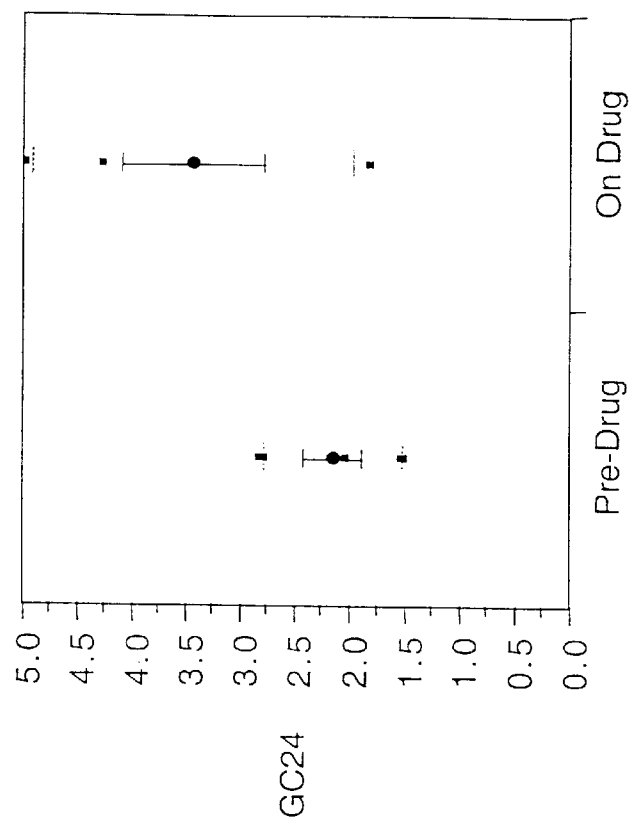
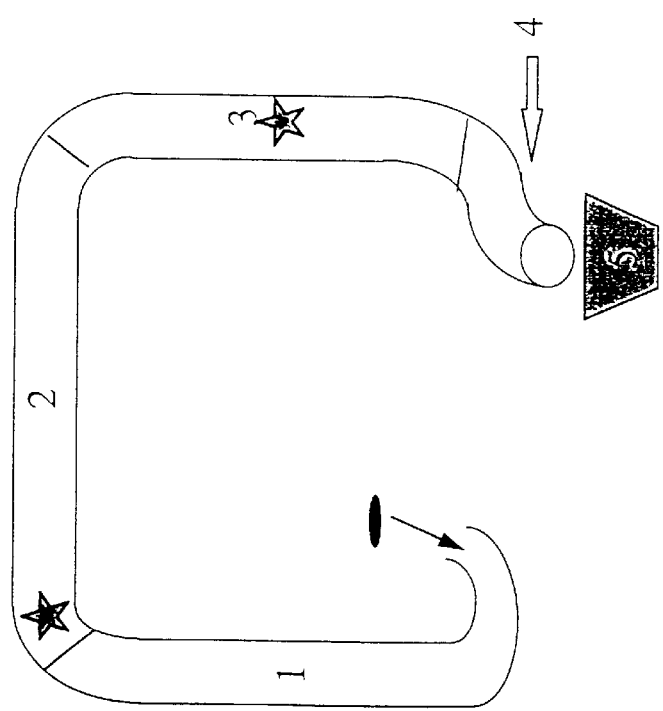
FIG. 7A

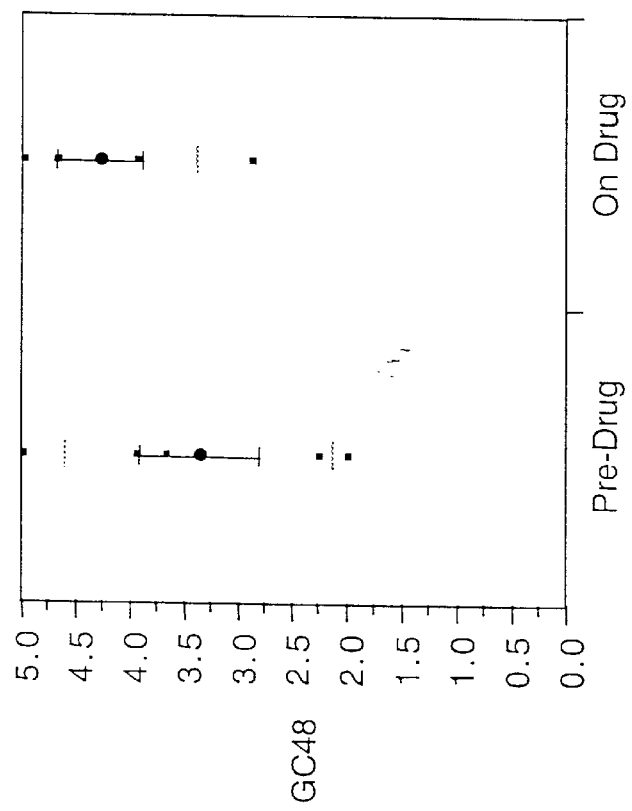
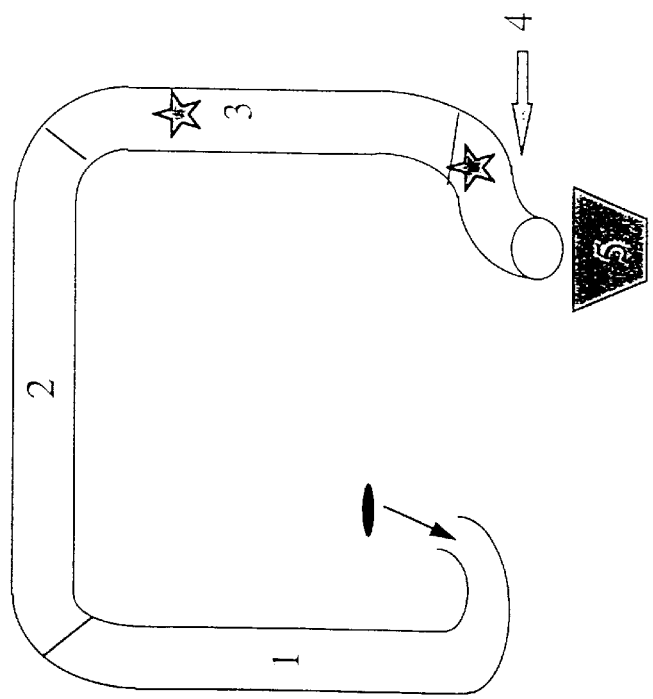
FIG. 7B

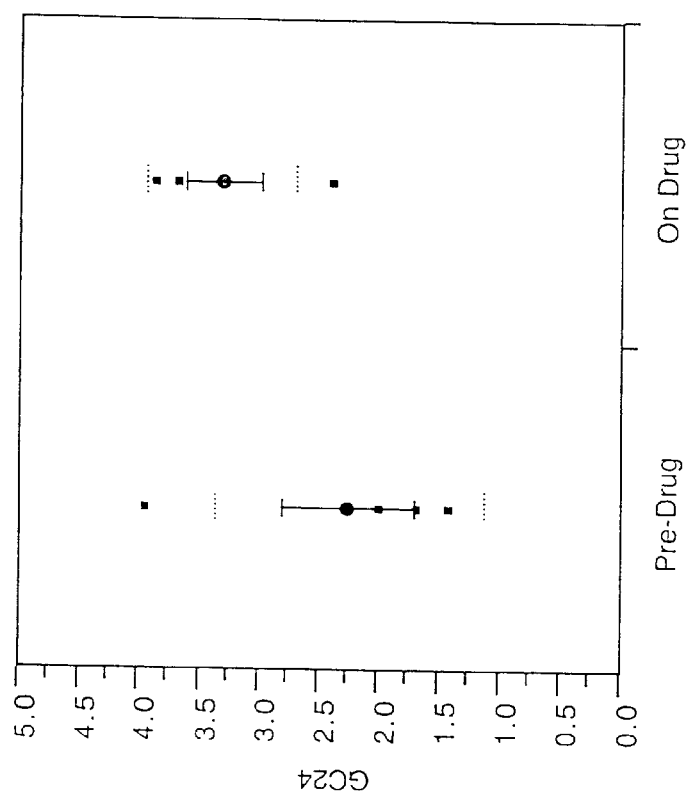
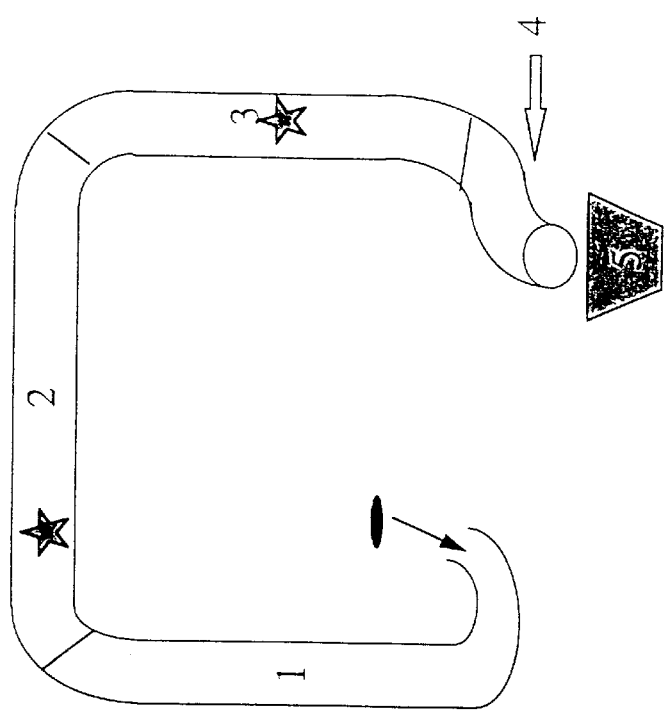
FIG. 7C

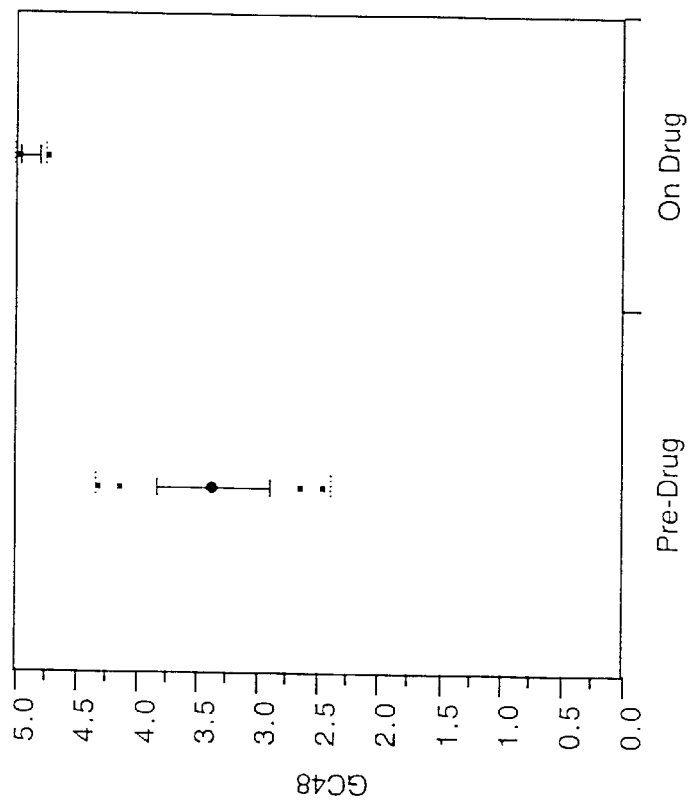
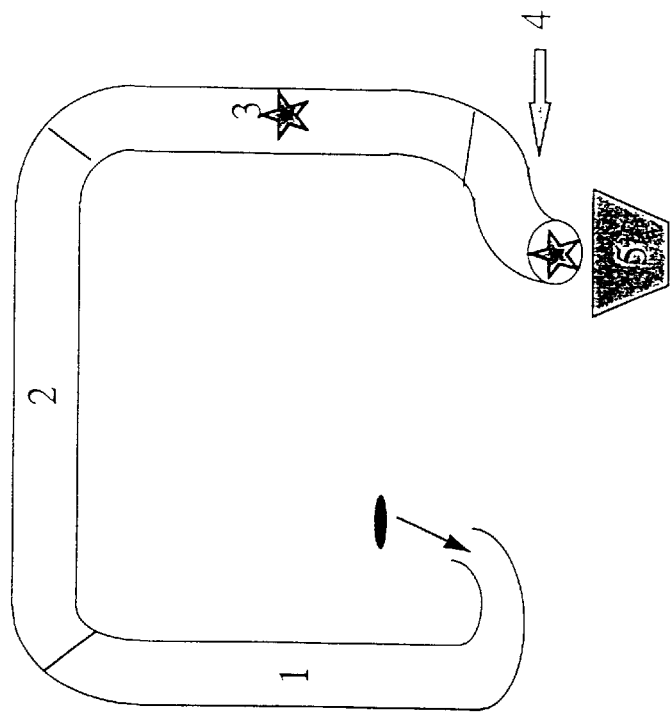
FIG. 7D

Investigator

Subjects

```
                         SEQUENCE LISTING

<160> NUMBER OF SEQ ID NOS: 1

<210> SEQ ID NO 1
<211> LENGTH: 120
<212> TYPE: PRT
<213> ORGANISM: Homo sapien

<400> SEQUENCE: 1

Met Tyr Ala Glu His Lys Ser His Arg Gly Glu Tyr Ser Val Cys Asp
 1               5                  10                  15

Ser Glu Ser Leu Trp Val Thr Asp Lys Ser Ser Ala Ile Asp Ile Arg
            20                  25                  30

Gly His Gln Val Thr Val Leu Gly Glu Ile Lys Thr Gly Asn Ser Pro
        35                  40                  45

Val Lys Gln Tyr Phe Thr Glu Thr Arg Cys Lys Glu Ala Arg Pro Val
    50                  55                  60

Lys Asn Gly Cys Arg Gly Ile Asp Asp Lys His Trp Asn Ser Gln Cys
65                  70                  75                  80

Lys Thr Ser Gln Thr Tyr Val Arg Ala Leu Thr Ser Glu Asn Asn Lys
                85                  90                  95

Leu Val Gly Trp Arg Trp Ile Arg Ile Asp Thr Ser Cys Val Cys Ala
            100                 105                 110

Leu Ser Arg Lys Ile Gly Arg Thr
        115                 120
```

METHODS OF USING A NEUROTROPHIN AND ITS ANALOGUES FOR THE TREATMENT OF GASTROINTESTINAL HYPOMOTILITY DISORDERS

1. FIELD OF INVENTION

This invention relates to methods of treating gastrointestinal hypomotility disorders. In particular, it relates to methods of using a neurotrophin and its analogues enhance gastrointestinal motility.

2. BACKGROUND OF INVENTION

Constipation, which is the passage of less than 3 bowel movements per week with excessive straining at least 25% of the time, is the most common gastrointestinal complaint in the United States, resulting in about 2 million annual visits to the clinic. (See, National Digestive Diseases Information Clearinghouse) In addition, Americans spend $725 million on laxatives each year without seeking medical help. According to the 1991 National Health Interview Survey, about 4.5 million people in the United States say they are constipated most or all of the time.

Constipation is one of the most common forms of gastrointestinal hypomotility disorders. Constipation also occurs with a number of other conditions including, but not limited to abdominal pain, abdominal cramps, irritable bowel syndrome, non-tropical sprue, megacolon associated with hypothyroidism, pseudo-obstruction of the gastrointestinal tract, colitis, hypomotility of the colon associated with diabetes mellitus, adult onset Hirschsprung's disease, neurological disorders, myopathic disorders, spinal cord injury, Parkinson's disease, jejunal-ileal bypass with secondary megacolon, cancer chemotherapy, critical illness including severe burns and other major stresses, with syndromes of depression, the post-operative state, and other pathological conditions.

Gastrointestinal hypomotility disorders also include disorders of the esophagus and gastric-motility including gastric emptying disorders such as diabetic gastroparesis and those that are associated with scleroderma.

Hypomotility may be associated with recurring bouts of hypermotility, the so-called intermittent hypomotility-hypermotility (or irritable bowel) syndrome. Clinical manifestations of this affliction include alternate bouts of constipation and diarrhea, abdominal distention, pains and cramps often relieved by passage of stool. Constipation may also occur in inflammation of gastrointestinal disorders such as ileitis, regional ententes ulcerative and other forms of colitis.

The digestive system functions to process nutrients and other food substances for efficient absorption by the cells of the body. When food is ingested, large particles are broken into smaller particles, enzymes are secreted to decompose food molecules, the products of the digestive action are absorbed, and unused residue is eliminated. In the alimentary canal of the digestive system, food and materials which are by-products of the digestive process are moved along by peristalsis—movement resulting from waves of alternate circular contraction and relaxation of the tubular structure of the canal by which the contents are propelled onward.

In the context of the present invention, motility consists of normal spontaneous coordinated distensions and contractions of the stomach, intestines, colon and rectum to move food through the gastrointestinal tract during the digestive process. Hypomotility disorders are those in which contractions are not occurring naturally or are abnormally slow, resulting in delayed passage of gut contents from stomach to anus. The disorder of unknown cause (idiopathic) in some 50% of the cases (Sleisenger et al., 1989, *Gastrointestinal Disease*, 4th ed., HBJ, Inc., Philadelphia, pp. 675–713).

Current forms of therapy for such hypomotility syndromes include treatment of the underlying disorder, dietary support, and use of prokinetic agents such as metoclopramide and cisapride (propulsid). In some instances, surgery may be required.

Although metoclopramide is most often prescribed among hypomotility patients, at least one study has indicated that this drug is effective in only 60% of patients with diabetic gastroparesis, and in only 25% of patients with prior gastric surgery (See e.g., Drug Evaluations, 6th ed., AMA, Chicago, 1986, p. 953). In addition, there is evidence that the effectiveness of metoclopramide dissipates with long term use. This appears to be the case at least where diabetes is the underlying disease (Schade et al., 1985, *Dig. Dis. Sci.*, 30:10–15 ). The long term value of the drug has not been established for treating gastric stasis which is either idiopathic or attributed to gastric ulcer.

Another reported disadvantage of metoclopramide therapy is that 20% to 30% of user patients experience side effects including drowsiness, restlessness, anxiety, tremor and muscle rigidity. (see, Sleisenger et al., Id.). In younger patients, metoclopramide frequently causes acute dystonic reactions such as torticollis, trismus, facial spasma, and opisthotonos. Id. In elderly patients, metoclopramide causes Parkinsonian reaction and irreversible tardive dyskinesia. Id. Other side effects of metoclopramide include hyperprolactinemia and subsequent impotence, gynecomastia, amenorrhea, or galactorrhea. Id.

Cisapride is a benzamide and its effects on the motility of the stomach and small bowel closely resemble those of metoclopramide; however, unlike metoclopramide, it also increases colonic motility and can cause diarrhea. (Brunton, 1990, *Agents Affecting Gastrointestinal Water Flux and Motility, Digestants, and Bile Acids*, in *Pharmacological Basis of Therapeutics*, Gilman et al., eds., p. 929, Pergamon Press, New York.) The mechanism of cisapride's gastrointestinal actions is poorly understood. Like metoclopramide, cisapride's actions are blocked by atropine and may involve the release of myenteric acetylcholine. Id. Cisapride appears to be devoid of dopaminergic blocking activity. Because it lacks central antidopaminergic effects, it does not influence the concentration of prolactin in plasma or cause extrapyramidal symptoms.

However, particularly in combination with other drugs (e.g., antifungals such as ketoconazole, itraconazole, and fluconazole; antibacterials such as erythromycin, clarithromycin, and troleandomycin; and HIV protease inhibitors ritonavir and indinavir), cisapride can cause serious ventricular arrhythmais and sudden death. (1990, *New Warnings Added to Cisapride Labeling*, JAMA 280:410). The common side effects of cisapride include abdominal cramping, diarrhea, and headache, which lead to drug discontinuation in 2% to 3% of patients.

Thus, there remains a need for improved compositions and methods for treating gastrointestinal hypomobility disorders such as constipation.

3. SUMMARY OF INVENTION

The present invention relates to the treatment of gastrointestinal hypomotility, particulary human acute and chronic constipation. More specifically, the invention relates to the use of a neurotrophin for the treatment of gastrointestinal hypomotility.

The invention is based, in part, on the inventor's discovery that neurotrophin-3 (NT-3) enhances gastrointestinal motility as measured by different parameters. The administration of NT-3 in humans improves stool frequency, colonic motility, gastric emptying and small bowel transit time, with minimal adverse side effects. Both healthy subjects and patients with constipation responded to NT-3 treatment.

One aspect of the present invention provides methods and compositions for the treatment of gastrointestinal hypomotility, typically, chronic constipation, obstipation, idiopathic abdominal distention, irritable bowel syndrome, megacolon associated with hypothyroidism, pseudo-obstruction of the gastrointestinal tract, hypomotility of the stomach and colon associated with diabetes mellitus, neurological disorders, myopathic disorders, spinal cord injury, Parkinson's disease, geriatric hypomotility disorders, jejunal-ileal bypass with secondary megacolon, hypomotility associated with cancer chemotherapy, hypomotility associated with severe burns and other major stresses, hypomotility associated with syndromes of depression, postoperative intestinal distension, and other pathological conditions, in a subject in need of such treatment. The subject is typically a mammal, and most preferably a human.

In some specific embodiments, NT-3 is used to treat patients experiencing acute constipation associated with orthopedic, gynecological, thoracic, and urological surgery or those experiencing constipation while in a coronary care unit or intensive care unit. In other embodiments, NT-3 is used to treat chronic constipation caused by enteric neuropathy/pseudo-obstruction, Parkinson's disease, paralysis due to multiple sclerosis, spinal cord injury (resulting in paraplegia or quadriplegia), chronic use of opiate pain killers, irritable bowel syndrome, and constipation in hospitalized/institutionalized patients. NT-3 produced by any method may be used for the practice of the invention; however, recombinant NT-3, such as the recombinant methionyl human NT-3 (r-metNT-3) described in Section 6, infra, is preferred.

In addition to the native NT-3, compositions of chimeras, such as NT-3 fusion polypeptides, peptides or biologically active fragments derived from the NT-3, NT-3 analogues or any other molecules which act as trkB or trkC receptor agonists are useful for the treatment of gastrointestinal hypomotility.

Furthermore, activating antibodies which activate the a NT-3 receptor, such as the trkC receptor, and imitate the effect of NT-3, are also useful for the treatment of gastrointerestinal hypomobility.

Also useful for the treatment of gastrointestinal hypomotility are molecules, preferably small molecules or small peptides, that can activate at any point the signal transduction pathway of NT-3.

In another aspect of the invention, methods and compositions are provided to treat diarrhea or other manifestations of gastrointestinal hypermotility. The subject is typically a mammal, and most preferably a human. Diagnosis of gastrointestinal hypermotility or diarrhea is known by those skilled in the art. The methods of this aspect of the invention comprise administering a therapeutically effective amount of pharmaceutical compositions of a NT-3 receptor antagonist, preferably a trkC receptor antagonist, a neutralizing antibody against a NT-3 receptor, preferably a trkC receptor neutralizing antibody, or a NT-3 neutralizing antibody in an acceptable pharmaceutical carrier, infra, to the subject in need, i.e., a subject afflicted with diarrhea, etc.

4. BRIEF DESCRIPTION OF THE FIGURES

FIG. 1 shows daily change in stool number in constipated patients after NT-3 administration.

FIGS. 2A and B show change in stool frequency after NT-3 administration.

FIGS. 3A and B show percent of days without stool by period before and after NT-3 administration.

FIGS. 5A and 5B show that NT-3 shortens gastric emptying half-time after NT-3 administration.

FIGS. 7A–7D show that NT-3 increases gastrointestinal motility as evidenced by advancement of geometric center of fecal bolus.

5. DETAILED DESCRIPTION OF THE INVENTION

Figure 1:
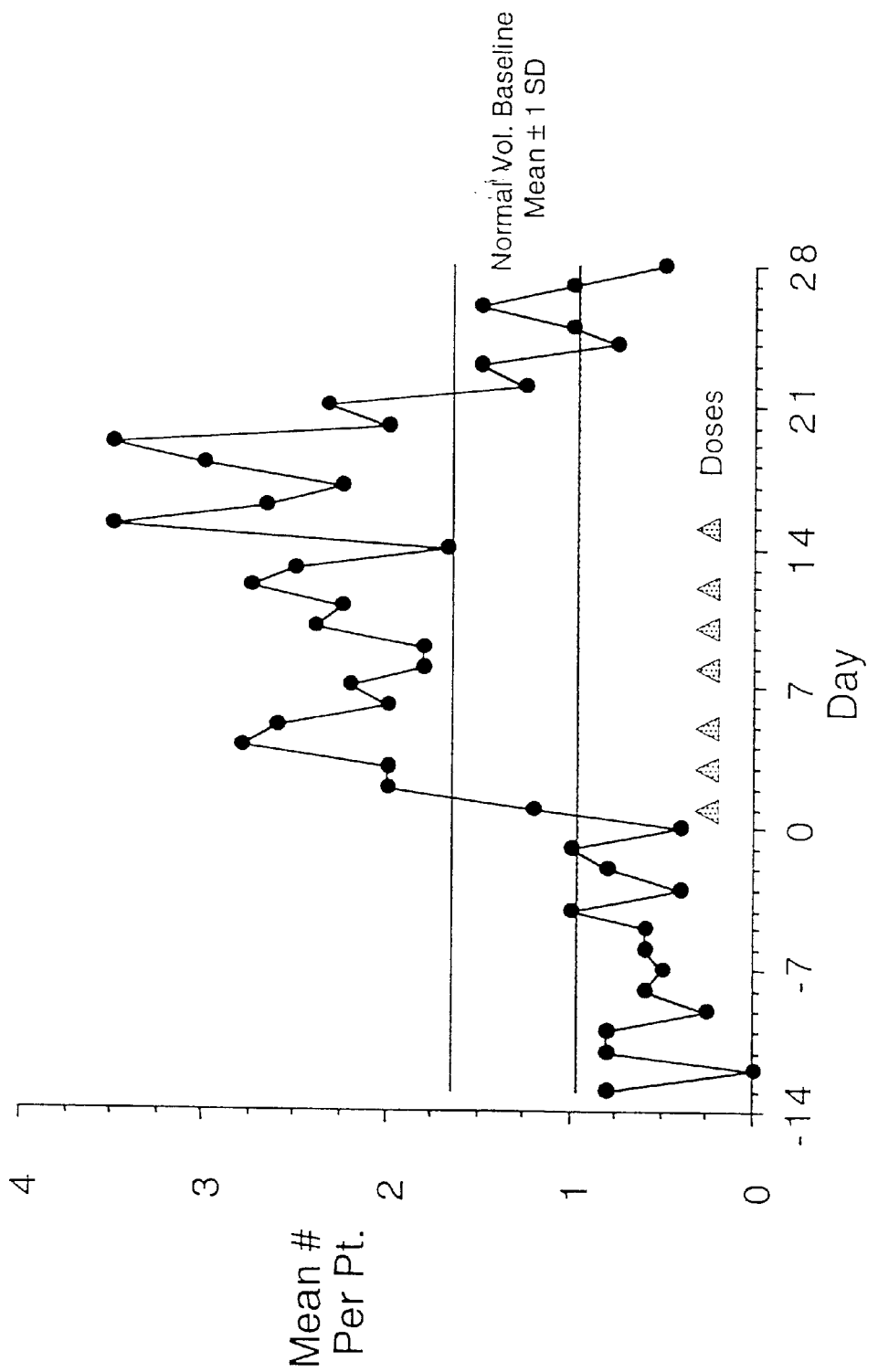

The present invention relates to the use of a neurotrophic factor, its analogues, mimetics, agonists and neurotrophin receptor activating antibodies for treating gastrointestinal hypomotility. Although the specific procedures and methods described herein are exemplified using a recombinant NT-3 for the treatment of constipation, they are merely illustrative for the practice of the invention. Analogous procedures and techniques, as well as those using functionally equivalent peptides and peptide analogues, mimetics, NT-3 receptor agonists and NT-3 receptor activating antibodies, which will be apparent to those of skill in the art based on the detailed disclosure provided herein, are also encompassed by the invention.

5.1 Neurotrophin-3 and its Uses in Treating Gastrointestinal Hypomotility

Neurotrophic factors are endogenous peptides that regulate the development, maintenance and survival of neurons. Generally, to be qualified as a neurotrophic factor, a peptide must be expressed at the right time by the target cells of neurons and trigger biochemical changes in the neurons on which it binds. In some instances, neurons secret neurotrophic factors that act upon the neurons in an autocine fashion (See, e.g., Glass and Yancopoulos, 1993, The Neurotrophins and Their Receptors, *Trends in Cell Biol.* 3:262–268; Lindsay et al., 1994, Prospectives. Neurotrophic Factors: From Molecule to man, *TINS* 17:182–190; all incorporated herein by reference for all purposes). The neurotrophic peptides may either be secreted by neuron cells or otherwise made available to neuron nucleus. Neurotrophic factors are generally small, soluble proteins with molecular weight ranging between 13 and 24 kDa and are often active as homodimers. There are three known families of neurotrophic factors: neurotrophins, neuropoietic cytokines and fibroblast growth factors, with members of each family sharing at least 50% sequence homology, and have affinities for particular classes of cell surface receptors.

Neurotrophin-3 (NT-3) is a member of the neurotrophin family of neurotrophic factors that are required for the differentiation and survival of specific neuronal subpopulations in both the central and the peripheral nervous systems (see, Eide et al., 1993, Neurotrophins and Their Receptors—current Concepts and Implications for Neurologic Disease, *Exp. Neurol.* 121:200–14; Snider et al., 1996, Neurotrophins Cause a New Sensation, *Neuron.* 16:229–32). The neurotrophin family is comprised of at least four proteins including NGF, BDNF, NT-3, and NT-4/5. These secreted neurotrophins are synthesized as prepropeptides that are proteolytically processed to generate the mature proteins. All neurotrophins have six conserved cysteine residues that are involved in the formation of three disulfide bonds and all share approximately 55% sequence identity at the amino acid level (Eide, Id).

Similar to NGF, bioactive NT-3 is predicted to be a non-covalently linked homodimer. The NT-3 cDNA encodes a 257 amino acid residue precursor protein with a signal peptide and a proprotein that is cleaved to yield the 119 amino acid residue mature NT-3. The amino acid sequence of mature NT-3 is identical in human, mouse and rat. NT-3 mRNA transcripts have been detected in the cerebellum, hippocampus, placenta, heart, skin, and skeletal muscle. NT-3 primarily activates the trkC receptor tyrosine kinase receptor (Lamballe et al. 1991, TrkC, a New Member of The Trk Family of Tyrosine Protein Kinases, is a Receptor for Neurotrophin-3, *Cell* 66:967–979). In addition, NT-3 can activate trkB kinase receptors in certain cell systems. NT-3 can also bind with low affinity to the low affinity p75 NGF receptor (see, Eide et al., 1993, Neurotrophins and Their Receptors—current Concepts and Implications for Neurologic Disease, *Exp. Neurol.* 121:200–14; Snider et al., 1996, Neurotrophins Cause a New Sensation, *Neuron.* 16:229–32).

NT-3 promotes the survival of cultured embryonic noradrenergic neurons of the locus coeruleus and in vivo survival of noradrenergic neurons of the locus coeruleus after 6-hydroxydopamine-induced lesions. NT-3 also promotes the survival and differentiation of cultured dopaminergic and cholinergic neurons from the developing substantia nigra, promotes the cholinergic phenotype of cultured rat motor neurons, increases survival of Purkinje cells, and stimulates neurite outgrowth in cultured hippocampal pyramidal neurons. In addition, NT-3 reduces neuronal activity by reducing the inhibitory GABAergic synaptic transmission by cultured cortical neurons.

During and after maturation, sensory neurons produce neutrophins which may act as autocrine survival factor for adult sensory neurons. For example, sensory neurons of the dorsal root ganglion (DRG) may be dependent upon the presence of autocrine brain-derived neurotrophic factors (BDNF) to survive (Acheson et al., 1995, A BDNF Autocrine Loop In Adult Sensory Neurons Prevents Cell Dealth, *Nature* (Lond.) 374:450–453). When the autocrine production of BDNF by DRG cells was reduced by treating the cells with BDNF antisense oligonucleotides, the neuronal survival was reduced by 35%. These neurons could be rescued by exogenous BDNF or NT-3.

Little is known about the responsiveness to and functions of neurotrophins in visceral afferent neurons and pregan-lionic parasympathetic neurons of the vagus nerve (Helke et al., 1998, Axonal Transport of Neurotrophins by Visceral Afferent and Efferent Neurons of the Vagus Nerve of the Rat, *J. Comp. Neurol,* 393:102–117). In one study, adult rat vagal neurons were shown to retrogradely accumulate specific members of the neurotrophin family via distinct receptor-mediated mechanisms, which suggests that neurotrophins may play an important role in the functions of vagal neurons. Id. However, the specific functions of neurotrophind in vagal neurons are still unknown.

Prior to the present invention, NT-3 had not been shown to have an effect on gastrointestinal motility. It is, therefore, a surprising discovery of the inventor that NT-3 enhances gastrointestinal motility. A human clinical trial shows that NT-3 is safe and effective for the treatment of gastrointestinal constipation (see Section 6, infra).

While it is not intended to be bound by the theory, it is believed that the actions of the NT-3 in promoting gastrointestinal motility may be associated with their activities on the vagus nerve and/or enteric neurons. The motor function of the gastrointestinal system depends upon the contraction of the smooth muscle cells and their integration and modulation by enteric and extrinsic nerves (Camilleri, 1998, Gastrointestinal Motility, in *Scientific American Medicine,* Dale and Federman, eds, Scientific American, Inc., New York). The major entrinsic nerve is the vagus nerve which has been shown to influence motor activity of gastric, small intestine and the colon (Camilleri, Id.) Therefore, it is possible that the effect of neurotrophins on gastrointestinal motility may be associated with their activity on the vagus or other enteric neurons that influence the motor activity of the gastrointestinal tract.

5.2 Therapeutic Indications and Methods of Treatment

In one aspect of the present invention, methods and compositions are provided for the treatment of gastrointestinal hypomotility, including but not limited to, chronic constipation, obstipation, idiopathic abdominal distention, abdominal pain, abdominal cramps, irritable bowel syndrome, megacolon associated with hypothyroidism, pseudo-obstruction of the gastrointestinal tract, hypomotility of the colon associated with diabetes mellitus, neurological disorders, myopathic disorders, geriatric hypomotility disorders, jejunal-ileal bypass with secondary megacolon, hypomotility associated with cancer chemotherapy, hypomotility associated with severe bums and other major stresses, hypomotility associated with syndromes of depression, Parkinson's disease and other neurodegenerative disorders, post-operative intestinal distension, and other pathological conditions, in a subject in need of such treatment. The subject is typically a mammal, and most preferably a human. Diagnosis of gastrointestinal hypomotility is known by those skilled in the art.

The methods of the invention comprise administering a therapeutically effective amount of pharmaceutical compositions of active NT-3, in an acceptable pharmaceutical carrier, see, infra, to the subject in need, i.e., a subject afflicted with gastrointestinal hypomotility. In some specific embodiments, NT-3 is used to treat patients experiencing acute constipation associated with orthopedic, gynecological, thoracic, and urological surgery or those experiencing constipation while in a coronary care unit or intensive care unit. In yet other embodiments, NT-3 are used to treat chronic constipation caused by enteric neuropathy/pseudo-obstruction, Parkinson's disease, paralysis due to multiple sclerosis, spinal cord injury (resulting paraplegia or quadriplegia), chronic use of opiates pain killers, irritable bowel syndrome, and constipation in hospitalized/ institutionalized patients.

In addition to the native NT-3, compositions of chimeras, such as NT-3 fusion protein, peptides or biologically active fragments derived from NT-3, NT-3 analogues or any other molecules which act as trkC receptor agonists are useful for the treatment of gastrointestinal hypomotility. Chimeric molecules comprising portions of NT-3 are likely to possess neurotrotrophic NT-3 activity, and in some cases exhibit a spectrum of activities larger than that of either parent molecule. The chimeric molecules may provide a number of advantages relative to naturally occurring NT-3. Chimeric neurotrophic factors may be used to provide, for example, the activities of two NT-3 molecules in a single molecule, or may serve as superagonists, thereby enabling an increased biological response at lower doses.

NT-3 analogues may be polypeptides, i.e., having amino acids bonded by peptidic linkages, or may be non-peptides, i.e., having amino acids not bonded by peptidic linkages, such as a substituted amide or an isostere of an amide or a peptidomimetic moiety. Also included within the definition of "NT-3 analogues" are forms of the various NT-3 peptides which are modified at their N- and/or C-terminus. "NT-3 agonist" as used herein means a molecule that is capable of binding to the NT-3 receptors, such as the trkC receptor, to initiate an action that is initiated by a physiological NT-3 molecule when it binds to its specific NT-3 receptors. Particularly preferred NT-3 agonists are NT-3 mimetics including peptidomimetics and small molecule mimetics.

Furthermore, activating antibodies which activate NT-3 receptors, such as the trkC receptor, and imitate the effect of NT-3 are also useful for the treatment of gastrointestinal hypomotility.

Also useful for the treatment of gastrointestinal hypomotility are molecules, preferably small molecules, that can activate at any point the signal transduction pathway of NT-3.

In another aspect of the invention, methods and compositions are provided to treat diarrhea and other manifestations of gastrointestinal hypermotility. The subject is typically a mammal, and most preferably a human. Diagnosis of gastrointestinal hypermotility is known by those skilled in the art. The methods comprise administering a therapeutically effective amount of pharmaceutical compositions of a NT-3 receptor antagonist, preferably a trkC receptor antagonist, a neutralizing antibody against a NT-3 receptor, preferably a trkC receptor neutralizing antibody, or a NT-3 neutralizing antibody in an acceptable pharmaceutical carrier, see, infra, to the subject in need, i.e., a subject afflicted with diarrhea. "NT-3 receptor antagonist" as used herein means an agent that is capable of combining with the NT-3 receptors, such as the trkC receptor, to inhibit, neutralize, impede or reverse, at least in part, an action of physiological NT-3 when it binds to NT-3 receptors, such as the trkC receptor, on cells. The term "neutralizing antibody against a NT-3 receptor" as used herein is intended to include those antibodies that block or diminish receptor activation including ligand receptor binding. The term "NT-3 neutralizing antibody" as used herein is intended to include those antibodies that diminish or abolish the physiological activities of a NT-3 molecule.

5.3 Methods of Making Neurotrophin-3 Peptides

NT-3 peptides of the invention or analogues thereof, may be prepared using virtually any art-known technique for the preparation of peptides and peptide analogues. One preferred method for making NT-3 peptides and their analogues or the biologically active portions of the NT-3 peptides or chimeric NT-3 molecules is the recombinant genetic engineering techniques.

5.3.1 Recombinant Synthesis

For recombinant production, a polynucleotide sequence encoding a linear form of the NT-3 peptide is inserted into an appropriate expression vehicle, i.e., a vector which contains the necessary elements for the transcription and translation of the inserted coding sequence, or in the case of an RNA viral vector, the necessary elements for replication and translation. The expression vehicle is then transfected into a suitable target cell which will express the peptide. Depending on the expression system used, the expressed peptide is then isolated by procedures well-established in the art. Methods for recombinant protein and peptide production are well known in the art (see, e.g., Maniatis et al., 1989, *Molecular Cloning a Laboratory Manual*, Cold Spring Harbor Laboratory, N.Y.; and Ausubel et al., 1989, *Current Protocols in Molecular Biology*, Greene Publishing Associates and Wiley Interscience, N.Y.).

A variety of host-expression vector systems may be utilized to express the NT-3 peptides described herein. These include, but are not limited to, microorganisms such as bacteria transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus or tobacco mosaic virus) or transformed with recombinant plasmid expression vectors (e.g., Ti plasmid) containing an appropriate coding sequence; or animal cell systems.

The expression elements of the expression systems vary in their strength and specificities. Depending on the host/ vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedron promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5 K promoter) may be used; when generating cell lines that contain multiple copies of expression product, SV40-, BPV- and EBV-based vectors may be used with an appropriate selectable marker.

In cases where plant expression vectors are used, the expression of sequences encoding the NT-3 peptides of the invention may be driven by any of a number of promoters. For example, viral promoters such as the 35S RNA and 19S RNA promoters of CaMV (Brisson et al., 1984, *Nature* 310:511–514), or the coat protein promoter of TMV (Takamatsu et al., 1987, *EMBO J*. 6:307–311) may be used;

alternatively, plant promoters such as the small subunit of RUBISCO (Coruzzi et al., 1984, *EMBO J.* 3:1671–1680; Broglie et al., 1984, *Science* 224:838–843) or heat shock promoters, e.g., soybean hsp17.5-E or hsp 17.3-B (Gurley et al., 1986, *Mol. Cell. Biol.* 6:559–565) may be used. These constructs can be introduced into plant cells using Ti plasmids, Ri plasmids, plant virus vectors, direct DNA transformation, microinjection, electroporation, etc. For reviews of such techniques see, e.g., Weissbach & Weissbach, 1988, *Methods for Plant Molecular Biology*, Academic Press, NY, Section VIII, pp. 421–463; and Grierson & Corey, 1988, *Plant Molecular Biology*, 2d Ed., Blackie, London, Ch. 7–9.

In one insect expression system that may be used to produce the NT-3 peptides of the invention, Autographa californica nuclear polyhidrosis virus (AcNPV) is used as a vector to express the foreign genes. The virus grows in *Spodoptera frugiperda* cells. A coding sequence may be cloned into non-essential regions (for example the polyhedron gene) of the virus and placed under control of an AcNPV promoter (for example, the polyhedron promoter). Successful insertion of a coding sequence will result in inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed. (See, e.g., Smith et al., 1983, *J. Virol.* 46:584; Smith, U.S. Pat. No. 4,215,051). Further examples of this expression system may be found in *Current Protocols in Molecular Biology*, Vol. 2, Ausubel et al., eds., Greene Publish. Assoc. & Wiley Interscience.

In mammalian host cells, a number of viral based expression systems may be utilized. In cases where an adenovirus is used as an expression vector, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing peptide in infected hosts. (e.g., See Logan & Shenk, 1984, *Proc. Natl. Acad. Sci.* (*USA*) 81:3655–3659). Alternatively, the vaccinia 7.5 K promoter may be used, (see, e.g., Mackett et al., 1982, *Proc. Natl. Acad. Sci.* (*USA*) 79:7415–7419; Mackett et al., 1984, *J. Virol.* 49:857–864; Panicali et al., 1982, *Proc. Natl. Acad. Sci.* (*USA*) 79:4927–4931).

In some preferred embodiments, mammalian gene expression vectors and mammalian host cells, such as CHO and COS7 cells are used to produce recombinant peptides. Mammalian gene expression systems are described, for example, in U.S. Pat. No. 5,266,490, issued on Nov. 30, 1993 to Davis et al.

Due to the inherent degeneracy of the genetic code, any DNA sequences which encode substantially the same or a functionally equivalent amino acid sequence NT-3, may be used in the practice of the invention for the expression of the polypeptide.

Altered nucleotide sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues, which result in a silent change thus producing a functionally equivalent peptide. Such conservative amino acid substitutions may be made on the basis of similarity in polarity, charge, solubility, hydrophobicity, hydrophilicity, and/or the amphipathic nature of the residues involved. For example, negatively charged amino acids include aspartic acid and glutamic acid; positively charged amino acids include lysine, histidine and arginine; amino acids with uncharged polar head groups having similar hydrophilicity values include the following: glycine, asparagine, glutamine, serine, threonine and tyrosine; and amino acids with non-polar head groups include alanine, valine, isoleucine, leucine, phenylalanine, proline, methionine and tryptophan.

In an alternate embodiment of the invention, the coding sequence of NT-3 could be synthesized in whole or in part, using chemical methods well known in the art. (See, e.g., Caruthers et al., 1980, *Nuc. Acids Res. Symp. Ser.* 7:215–233; Crea and Horn, 180, *Nuc. Acids Res.* 9(10) :2331; Matteucci and Caruthers, 1980, *Tetrahedron Letter* 21:719; and Chow and Kempe, 1981, *Nuc. Acids Res.* 9(12):2807–2817). Alternatively, the peptide itself could be produced using chemical methods to synthesize an amino acid sequence in whole or in part. For example, peptides can be synthesized by solid phase techniques, cleaved from the resin, and purified by preparative high performance liquid chromatography (See Creighton, 1983, *Proteins Structures and Molecular Principles*, W.H. Freeman and Co., N.Y. pp. 50–60). The composition of the synthetic polypeptides may be confirmed by amino acid analysis or sequencing (e.g., the Edman degradation procedure; see Creighton, 1983, *Proteins, Structures and Molecular Principles*, W.H. Freeman and Co., N.Y., pp. 34–49).

In addition, NT-3 analogues can be chemically synthesized. Nonclassical amino acids or chemical amino acid analogs can be introduced as a substitution or addition into the sequence. Non-classical amino acids include, but are not limited to, the D-isomers of the common amino acids, α-amino isobutyric acid, 4-aminobutyric acid, Abu, 2-amino butyric acid, γ-Abu, ∈-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

In a preferred embodiment, recombinant methionyl-neurotrophin-3 (r-metHuNT-3) is used for the treatment of gastrointestinal hypomotility in human. R-metHuNT-3 is a protein produced in Escherichia coli into which a plasmid containing a coding sequence for human NT-3 has been inserted. The *E coli* production system uses a synthetic gene. The r-metHuNT-3 has an amino acid sequence identical to native human NT-3 with the addition of an amino terminal methionine. Cells expressing r-metHuNT-3 are grown in culture under defined and controlled conditions. Harvesting of the cells yields a crude paste containing r-metHuNT-3. The protein sequence consists of 119 amino acids plus an amino terminal methionine with a dimeric molecular mass of approximately 27 kilodaltons. The structural formula of r-metHuNT-3 is given below:

| Primary Amino Acid Sequence of r-metHuNT-3 | | | | | | | | | | | |
|---|---|---|---|---|---|---|---|---|---|---|---|
| NH2-Met | Tyr | Ala | Glu | His | Lys | Ser | His | Arg | Gly | Glu | 10 |
| | Tyr | Ser | Val | Cys | Asp | Ser | Glu | Ser | Leu | Trp | 20 |
| | Val | Thr | Asp | Lys | Ser | Ser | Ala | Ile | Asp | Ile | 30 |
| | Arg | Gly | His | Gln | Val | Thr | Val | Leu | Gly | Glu | 40 |
| | Ile | Lys | Thr | Gly | Asn | Ser | Pro | Val | Lys | Gln | 50 |
| | Tyr | Phe | Try | Glu | Thr | Arg | Cys | Lys | Glu | Ala | 60 |
| | Arg | Pro | Val | Lys | Asn | Gly | Cys | Arg | Gly | Ile | 70 |
| | Asp | Asp | Lys | His | Trp | Asn | Ser | Gln | Cys | Lys | 80 |
| | Thr | Ser | Gln | Thr | Tyr | Val | Arg | Ala | Leu | Thr | 90 |
| | Ser | Glu | Asn | Asn | Lys | Leu | Val | Gly | Trp | Arg | 100 |
| | Trp | Ile | Arg | Ile | Asp | Thr | Ser | Cys | Val | Cys | 110 |
| | Ala | Leu | Ser | Arg | Lys | Ile | Gly | Arg | Thr-COOH | | 119 |
| (SEQ ID NO:1) | | | | | | | | | | | |

Other expression systems for producing the NT-3 peptides of the invention will be apparent to those having skill in the art.

One of skill in the art would appreciate that the methods described above are useful for making chimeric NT-3 molecules. Methods for making multitrophic and multifunctional chimeric neurotrophic factors are also described, for example, in U.S. Pat. No. 5,512,661, issued on Apr. 30, 1996 to Shooter et al. and U.S. Pat. No. 5,169,764, issued on Dec. 8, 1992 to Shooter et al.

5.3.2 Purification Methods

The NT-3 peptides, NT-3 chimeric molecules and peptide analogues of the invention can be purified by art-known techniques such as high performance liquid chromatography, ion exchange chromatography, gel electrophoresis, affinity chromatography and the like. The actual conditions used to purify a particular peptide or analogue will depend, in part, on factors such as net charge, hydrophobicity, hydrophilicity, etc., and will be apparent to those having skill in the art.

For affinity chromatography purification, any antibody which specifically binds the NT-3 peptides or peptide analogues may be used. For the production of antibodies, various host animals, including but not limited to rabbits, mice, rats, etc., may be immunized by injection with a linear peptide. The peptide may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum*.

Monoclonal antibodies to a peptide may be prepared using any technique which provides for the production of antibody molecules by continuous cell lines in culture. These include but are not limited to the hybridoma technique originally described by Koheler and Milstein, 1975, *Nature* 256:495–497, the human B-cell hybridoma technique, Kosbor et al., 1983, *Immunology Today* 4:72; Cote et al., 1983, *Proc. Natl. Acad. Sci. U.S.A.* 80:2026–2030 and the EBV-hybridoma technique (Cole et al., 1985, *Monoclonal Antibodies and Cancer Therapy*, Alan R. Liss, Inc., pp. 77–96 (1985)). In addition, techniques developed for the production of "chimeric antibodies" (Morrison et al., 1984, *Proc. Natl. Acad. Sci. U.S.A.* 81:6851–6855; Neuberger et al., 1984, *Nature* 312:604–608; Takeda et al., 1985, *Nature* 314:452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce peptide-specific single chain antibodies.

When r-metHuNT-3 is produced, extracted from recombinant cells, and refolded, it is purified by a series of processing and chromatography steps. The resulting purified r-metHuNT-3 is formulated in an aqueous buffer before undergoing sterile filtration, dispensing into vials, and lyophilization.

Cell culture proliferation assays are performed to assess the biological activity of purified preparations of r-metHuNT-3. High performance liquid chromatography (HPLC), and sodium dodecylsulphate-polyacrylamide gel electrophoresis (SDS-PAGE) (reduced and nonreduced) are among the tests done to characterize each lot.

Criteria for release of r-metHuNT-3 for human uses are stringent. The product must be sterile, biologically active, nonpyrogenic, and not less than 95% pure by SDS-PAGE analysis. It must pass the United States Pharmacopeia (USP) rabbit pyrogen test, the Limulus amebocyte lysate assay, and the general safety test (21 C.F.R. §610.11).

Purified r-metHuNT-3 is a nonglycosylated, noncovalent dimeric molecular species with a molecular mass of approximately 27 kilodaltons. SDS-PAGE, gel filtration HPLC, reversed phase HPLC, peptide mapping, and amino acid sequence analysis all confirm the identity and purity of the r-metHuNT-3 protein.

5.3.3. Modification of NT-3 and Analogues Thereof

In some preferred embodiments, NT-3 and analogues thereof, particularly recombinant NT-3 peptides, are chemically modified. The chemical moieties most suitable for modification include water soluble polymers. A water soluble polymer is desirable because the peptide to which it is attached does not precipitate in an aqueous environment, such as a physiological environment.

Preferably, the polymer will be pharmaceutically acceptable for the preparation of a therapeutic product or composition. One skilled in the art will be able to select the desired polymer based on such considerations as whether the polymer/protein conjugate will be used therapeutically, and if so, the desired dosage, circulation time, resistance to proteolysis, and other considerations. The effectiveness of the derivatization may be ascertained by administering the derivative, in the desired form (i.e., by osmotic pump, or, more preferably, by injection or infusion, or, further formulated for oral, pulmonary or other delivery routes), and determining its effectiveness.

Suitable water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof.

Polyethylene glycol propionaldehyde may have advantages in manufacturing due to its stability in water. The polymer may be of any molecular weight, and may be branched or unbranched. For polyethylene glycol, the preferred molecular weight ranges from about 2 kDa to about 100 kDa for ease in handling and manufacturing (the term "about" indicating that in preparations of polyethylene glycol, some molecules will weigh more, some less, than the stated molecular weight). Other sizes may be used, depending on the desired therapeutic profile (e.g., the duration of sustained release desired, the effects, if any on biological activity, the ease in handling, the degree or lack of antigenicity and other known effects of polyethylene glycol on a therapeutic protein or variant).

The number of polymer molecules so attached may vary, and one skilled in the art will be able to ascertain the effect on function. One may mono-derivatize, or may provide for a di-, tri-, tetra- or some combination of derivatization, with the same or different chemical moieties (e.g., polymers, such as different weights of polyethylene glycols). The proportion of polymer molecules to protein (or peptide) molecules will vary, as will their concentrations in the reaction mixture. In general, the optimum ratio (in terms of efficiency of reaction in that there is no excess unreacted protein or polymer) will be determined by factors such as the desired degree of derivatization (e.g., mono-, di-, tri-, etc.), the molecular weight of the polymer selected, whether the polymer is branched or unbranched, and the reaction conditions. The polyethylene glycol molecules (or other chemical moieties) should be attached to the protein with consideration of effects on functional or antigenic domains of the protein. There are a number of attachment methods available to those skilled in the art. See for example, Magal, Method for Treating Sensorineural Hearing Using Glial Cell-Line-Derived Neurotrophic Factor (GDNF) Protein Product, U.S. Pat. No. 5,837,681, issued on Nov. 17, 1998, incorporated herein by reference for all purposes.

For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residue. Those having a free carboxyl group may include aspartic acid residues, glutamic acid residues, and the C-terminal amino acid residue. Sulfhydryl groups may also be used as a reactive group for attaching the polyethylene glycol molecule(s). For therapeutic purposes, attachment at an amino group, such as attachment at the N-terminus or lysine group is preferred. Attachment at residues important for receptor binding should be avoided if receptor binding is desired.

Pegylation of NT-3 peptides and analogues thereof may be carried out by any of the pegylation reactions known in the art. Methods for determination of other reaction parameters, such as solvent, reaction times, temperatures, etc., and means of purification of products, are well known to one skilled in the art and is described in, for example, U.S. Pat. No. 5,837,681, previously incorporated by reference for all purposes.

5.4. Antibodies to NT-3 Receptors

Antibodies directed to the NT-3 receptors, preferably, the trkC receptor, are useful for treating gastrointestinal hypomotility or hypermotility. In a preferred embodiment, an activating anti-NT-3 receptor antibody is used to treat gastrointestinal hypomotility. Alternatively, a neutralizing anti-NT-3 receptor antibody or a NT-3 neutralizing antibody is used to treat diarrhea or other manifestations of gastrointestinal hypermotility.

Antibodies against the trkC receptor are particularly preferred, because NT-3 is believed to be the preferred binding ligand for the trkC receptor. (Lamballe et al. 1991, TrkC, a New Member of The Trk Family of Tyrosine Protein Kinases, Is a Receptor For Neurotrophin-3, *Cell* 66:967–979). However, antibodies against other NT-3 receptors are also useful for the methods of the invention.

Methods for making anti-NT-3 receptor antibodies are well known to one skilled in the art. For example, immunoglobulins which activate or block trk receptors are described in Gary, et al., Antibodies That Mimic Actions of Neurotrophins, U.S. Pat. No. 5,753,225, issued on May 19, 1998 and Presta et al., Human Trk Receptors and Neurotrophic Factor Inhibitors, U.S. Pat. No. 5,844,092, issued on Dec. 1, 1998, both incorporated herein by reference for all purposes.

Various procedures known in the art may be used for the production of antibodies to epitopes of the naturally-occurring, synthetic and recombinantly produced NT-3 receptor protein. Such antibodies include, but are not limited, to polyclonal, monoclonal, chimeric, humanized, single chain, anti-idiotypic, antigen-binding antibody fragments and fragments produced by a variable region expression library.

For the production of antibodies, various host animals may be immunized by injection with the recombinant or naturally NT-3 receptor protein, fusion protein or peptides, including but not limited to rabbits, mice, rats, hamsters, and the like. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum*.

Monoclonal antibodies to NT-3 receptors may be prepared by using any technique which provides for the production of antibody molecules by continuous cell lines in culture. These include but are not limited to the hybridoma technique originally described by Kohler and Milstein, (*Nature* 1975, 256:495–497), the human B-cell hybridoma technique (Kosbor et al., 1983, *Immunology Today*, 4:72; Cote et al., 1983, *Proc. Natl. Acad. Sci*., 80:2026–2030) and the EBV-hybridoma technique (Cole et al., 1985, *Monoclonal Antibodies and Cancer Therapy*, Alan R. Liss, Inc., pp. 77–96). Such antibodies may be of any immunoglobulin class including, but not limited to, IgG, IgM, IgE, IgA, IgD and any subclass thereof. The hybridoma producing the monoclonal antibodies of this invention may be cultivated in vitro or in vivo.

In addition, techniques developed for the production of "chimeric antibodies" (Morrison et al., 1984, *Proc. Natl. Acad. Sci.*, 81:6851–6855; Neuberger et al., 1984, *Nature*, 312:604–608; Takeda et al., 1985, *Nature* 314:452–454; U.S. Pat. Nos. 4,816,567 and 4,816,397) by splicing the genes from a mouse antibody molecule of appropriate antigen specificity together with genes from a human antibody molecule of appropriate biological activity can be used. Humanized antibodies may be generated according to the methods described in U.S. Pat. Nos. 5,693,762; 5,585,089 and 5,565,332.

Alternatively, techniques described for the production of single chain antibodies (U.S. Pat. No. 4,946,778; Bird, 1988, *Science* 242:423–426; Huston et al., 1988, *Proc. Natl. Acad. Sci. USA* 85:5879–5883; and Ward et al., 1989, *Nature* 334:544–546) can be adapted to produce single chain antibodies against gene products of interest. Single chain antibodies are formed by linking the heavy and light chain fragments of the Fv region via an amino acid bridge, resulting in a single chain polypeptide.

Hybridomas may be screened using enzyme-linked immunosorbent assays (ELISA) or radioimmunoassays in order to detect cultures secreting antibodies specific for refolded recombinant NT-3 receptors. Subsequent testing may use recombinant NT-3 receptor fragments to identify the specific portion of the NT-3 receptor molecule with which a monoclonal antibody binds. Additional testing may be used to identify monoclonal antibodies with desired functional characteristics such as staining of histological sections, immunoprecipitation or Western blotting of NT-3 receptors, or neutralization of NT-3 receptor activity. Determination of the monoclonal antibody isotype may be accomplished by ELISA, thus providing additional information concerning purification or function.

Antibody fragments which recognize specific binding sites of NT-3 receptors may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, *Science*, 246:1275–1281; U.S. Pat. Nos. 5,223,409; 5,403,484 and 5,571,698) to allow rapid and easy identification of monoclonal Fab fragments with the desired specificity to NT-3 receptors. Antibody constant regions can be altered by molecular manipulations to modify their effector functions (U.S. Pat. No. 5,624,821). The complementarity-determining regions (CDR) of an antibody can be identified, and synthetic peptides corresponding to such regions are used to mediate antigen binding (U.S. Pat. No. 5,637,677).

In preferred embodiments, humanized antibodies are used to treat human patients. Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers; Jones et al., 1986, *Nature* 321:522–525; Riechmann et al., 1988 *Nature* 332:323–327; Verhoeyen et al., 1988, *Science* 239:1534–1536, by substituting rodent CDRs or CDR sequences for the corresponding sequences of a human antibody. Accordingly, such "humanized" antibodies are chimeric antibodies, wherein substantially less than an intact human variable domain has been substituted by the corresponding sequence from a non-human species. In practice, humanized antibodies are typically human antibodies in which some CDR residues and possibly some framework (FR) residues are substituted by residues from analogous sites in rodent antibodies.

It is important that antibodies be humanized with retention of high affinity for the receptors and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved.

Human monoclonal antibodies can be made by the hybridoma method. Human myeloma and mouse-human heteromyeloma cell lines for the production of human monoclonal antibodies have been described, for example, by Kozbor, 1984, *J. Immunol.* 133:3001, and Brodeur et al., 1987, *Monoclonal Antibodies Production Techniques and Applications*, pp.51–63 (Marcel Dekker, Inc., New York).

Transgenic animals (e.g. mice) that are capable, upon immunization, of producing a repertoire of human antibodies in the absence of endogenous immunoglobulin production may also be used to produce human antibodies. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al., 1993, *Proc. Natl. Acad. Sci. USA* 90:2551–255; Jakobovits et al., 1993, *Nature*, 362: 255–258.

Alternatively, the phage display technology (McCafferty et al., 1990, *Nature* 348:552–553) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimicks some of the properties of the B-cell. Phage display can be performed in a variety of formats; see, e.g. Johnson et al., 1993, *Current Opinion in Structural Biology* 3:564–571.

5.5. Formulations

Active ingredients for the treatment of gastrointestinal hypomotility include NT-3 and analogues thereof, NT-3 mimetics, NT-3 receptor activating antibodies and other NT-3 agonists. Active ingredients for the treatment of diarrhea and other manifestation of diarrhea include NT-3 receptor antagonists, anti-NT-3 receptor neutralizing antibodies and NT-3 neutralizing antibodies.

The active ingredients may be administered to a subject per se or in the form of a pharmaceutical composition. Pharmaceutical compositions comprising the compounds of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the active ingredients into preparations which can be used pharmaceutically. Proper formulation is dependent upon the route of administration chosen. The active ingredients may be administered by methods including, but not limited to topical administration, systemic administration, transmucosal administration, oral administration, and administration by inhalation. In some preferred embodiments, the active ingredients are administrated by injections using syringes, spring- or gas driven syringe devices, or needle less injector systems. In some other embodiments, the active ingredients are administrated using subcutaneously implanted sustained devices.

For topical administration the active ingredients may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration. For injection, the compounds of the invention may be formulated in aqueous solutions, preferably in physiologically compatible buffers such as Hanks's solution, Ringer's solution, or physiological saline buffer. The solution may contain formulatory agents such as suspending, stabilizing and/or dispersing agents. Alternatively, the compounds may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, the compositions can be readily formulated by combining the active ingredients with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated.

For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); polymeric carriers such as polylcatic/polyglycolic acid, granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the active ingredients may take the form of tablets, lozenges, etc. formulated in conventional manner.

For administration by inhalation, the active ingredients for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The active ingredients may also be formulated in rectal or vaginal compositions such as suppositories or retention enemas, e.g, containing conventional suppository bases such as cocoa butter or other glycerides.

In addition to the formulations described previously, the active ingredients may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver active ingredients of the invention. Certain organic solvents such as dimethylsulfoxide also may be employed, although usually at the cost of greater toxicity.

Additionally, the compounds may be delivered using a sustained-release system, such as semipermeable matrices of solid polymers containing the therapeutic agent. Various sustained-release materials have been established and are well known by those skilled in the art. For example, sustained-release formulations of steroids and peptides such as a luteinizing hormone-releasing hormone analogue have been developed using the biodegradable polymers of DL-lactic co-glycolic acid (PLGA). (See, Hutchinson et al., 1985, Biodegradable Polymers for Sustained Release of Peptides, *Biochem. Soc. Trans.* 13:520–523; Ogawa et al., 1988, in Vivo Release Profiles of Leiprolide Acetate from Microcapsules Pepared with Polylactic Acids or Copoly (lactic/glycolic) Acids and in Vivo Degradation of These Polymers. Chem. Pharm. Bull. 36:2576–2581; Sanders et al. 1986, Prolonged Controlled Release of Nafarelin, a Luteinizing Hormone-releasing Hormone Analogue from Biodegradable Polymeric Implants: Influence of Composition and Molecular Weight of Polymer, *J. Pharm. Sci.* 75:356–360; Cowsar et al., 1985, Poly(lactide-co-glycolid) Microcapsule for Controlled Release of Steroids, *Methods in Enzymology* 112:101–655, all incorporated by reference for all purposes). An injectable sustained-release form of growth hormone was developed by stabilizing and encapsulating the protein into biodegradable microsphere using a cryogenic process. (Johnson, et al., 1996, A Month Long Effect from a Single-injection of Microencapsulated Human Hormone, *Nature-Medicine* 2:795–799.) This process is useful for encapsulating any protein that can be stabilized as powder. Methods for making microspheres containing polymer-biological agent mixture are also described, for example, in Gombotz, et al., Very Low Temperature Casting of Controlled Release Microspheres, U.S. Pat. No. 5,019,400, issued on May 28, 1991, incorporated herein by reference for all purposes.

In a preferred embodiment, active ingredients, preferably, a recombinant NT-3, are microencapsulated by combining chitosan with copolymerized lactic and glycolic acid for sustained release. In this embodiment, a water soluble active ingredient is dissolved together with emulsifying agents (alginate, gelatine, chirosan) and the polymer is dissolved in $CH_3Cl_2$. Sonication of the primary emulsion and addition of the outer water phase results in formation of a complex emulsion. Elimination of volative solvent can be achieved in a continuous or interrupted manner at room temperature and/or at reduced pressure. The final product is obtained after multiple washing and vacuum drying. This encapsulation method is described in more detail in Maysinger et al., 1996, Microencapsulated Ciliary Neurotrophic Factor: Physical Properties and Biological Activities, *Dev. Neurol.* 138:177–188.

Depending on the chemical nature and the biological stability of the therapeutic reagent, additional strategies for protein stabilization may be employed. As the active ingredients of the invention may contain charged side chains or termini, they may be included in any of the above-described formulations as the free acids or bases or as pharmaceutically acceptable salts. Pharmaceutically acceptable salts are those salts which substantially retain the antimicrobial activity of the free bases and which are prepared by reaction with inorganic acids. Pharmaceutical salts tend to be more soluble in aqueous and other protic solvents than are the corresponding free base forms.

In preferred embodiments, r-metHuNT-3 is prepared as a lyophilized powder that is to be reconstituted with sterile water for injection at concentrations of 15 mg/mL and 5 mg/mL. The reconstituted solution is buffered at approximately pH 5.0 with 10 mM histidine and contains 0.5% sucrose and 4.5% mannitol. In the preferred embodiment, r-metHuNT-3 contains no preservative.

5.6. Dosage

The compositions of the invention will generally be used in an amount effective to achieve the intended purpose, i.e., treating gastrointestinal hypomotility or diarrhea. To treat gastrointestinal hypomotility, NT-3, NT-3 analogues, NT-3 mimetics, or NT-3 activating anti-NT-3 antibodies or pharmaceutical compositions thereof, are administered or applied in a therapeutically effective amount. "Therapeutically effective amount" means an amount that is effective at ameliorating or preventing the symptoms of the patient being treated. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans. Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the compounds which are sufficient to maintain therapeutic effect. In some preferred embodiments, dosage of NT-3 in the range of 25–500 µg/kg body weight is administered subcutaneously one to seven, preferably three, times per week. More preferably, the dosage is around 100–300 µg/kg, administered subcutaneously one to seven, preferably three, times per week. In cases of local administration or selective uptake, the effective local concentration of the compounds may not be related to plasma concentration. One having skill in the art will be able to optimize therapeutically effective local dosages without undue experimentation.

The amount of active ingredients administered will, of course, be dependent on the subject being treated, on the subject's weight, the severity of the affliction, the manner of administration and the judgment of the prescribing physician.

The therapy may be repeated intermittently while symptoms are detectable or even when they are not detectable. The therapy may be provided alone or in combination with other drugs.

5.7. Toxicity

Preferably, a therapeutically effective dose of the compounds described herein will provide therapeutic benefit without causing substantial toxicity.

Toxicity of the compounds described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in human. The dosage of the compounds described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: *The Pharmacological Basis of Therapeutics*, Ch.1, p.1).

In studies using NT-3, single doses of NT-3 up to 500 µg/kg produced no complaints of diarrhea, and daily doses of up to 250 µg/kg/day for seven days produced diarrhea in a few patients.

The invention having been described, the following examples are offered by way of illustration and not limitation.

6. EXAMPLE

NT-3 Accelerates Small Bowel and Colonic Transit in Healthy Humans and Patients with Constipation This example demonstrates that recombinant NT-3 is a safe and effective treatment for constipation in humans. It also shows that NT-3 enhances human gastrointestinal motility.

6.1. Materials and Methods

In this study, six healthy volunteers were assigned to group 1. Group 2 included six patients with self-reported constipation (as defined in Section 2, supra) in whom evacuation disorders were excluded. Both groups were subjected to an open-label study of 6 weeks with 2 weeks of lead-in, two weeks of treatment and two weeks of washout. During the two week treatment period, participants received a dose of 300 µg/kg recombinant-metHuNT-3 (r-metHuNT-3) three times per week (t.i.w.) subcutaneously for a total of seven doses. Recombinant-metHuNT-3 was supplied as a sterile, lyophilized powder for reconstitution with sterile water for injection at concentrations of 5 mg/mL and 15 mg/mL. The reconstituted solution was buffered to approximately pH 5.0 with 10 mM histidine and this final solution contained 0.5% sucrose and 4.5% mannitol.

Gastrointestinal transit in the two groups was measured in the following ways. Colonic transit was measured over 48 hr after the lead-in and treatment periods using a delayed-release capsule containing 0.1 mCi of $^{111}InCl_3$-labeled activated charcoal. Gastric and small bowel transit were measured using an egg meal labeled with 1.0 mCi of $^{99m}Tc$-sulfur colloid. Study subjects were scanned for distribution of the isotopes in their gastrointestinal tract by a method as described in Camilleri, 1992, Towards a Relatively Inexpensive, Noninvasive, Accurate Test for Colonic Motility Disorders, *Gastroenterology* 103:36–42. For each scan, the amounts of isotopes in the stomach their gastrointestinal tract by a method as described in Camilleri, 1992, Towards a Relatively Inexpensive, Noninvasive, Accurate Test for Colonic Motility Disorders, *Gastroenterology* 103:36–42. For each scan, the amounts of isotopes in the stomach and 4 colonic regions (ascending, transverse, descending, combined sigmoid and rectum) were measured. In addition, stool frequency, consistency and ease of passage were recorded daily.

The change in each measurement (transit parameters or stool diary measures) was obtained by substracting the pretreatment value from the end-of-treatment value for each subject. The changes in each measurement for each group of subjects (healthy volunteers or constipated patients) were tested against a null hypothesis of zero change using paired t-test and paired Wilcoxon signed-rank tests.

6.2. Results

Healthy volunteers and subjects with constipation were treated with recombinant NT-3, and a variety of parameters of gastrointestinal mobility were measured. Generally, NT-3 caused an increase in stool frequency, ease of passage and softening in stool consistency in both groups of patients. The observed effect was not characterized as diarrhea in most cases. The onset of NT-3 induced effects in bowel function was rapid (within 24 hours) and lasted for several days after treatment ended.

Increase of stool frequency Data obtained from five of the six constipated patients and four of the six healthy volunteers are summarized in FIGS. 1–13. FIG. 1 shows that the stool number of constipated patients increased during and shortly after the treatment period. The increase of stool number by NT-3 treatment is also demonstrated in FIG. 2A which shows the weekly stool number before and during NT-3 treatment. Each line denotes one patient. The effect of NT-3 is not limited to constipated patients. FIG. 2B shows that NT3 treatment also increased weekly stool number in normal healthy volunteers.

FIGS. 3A and 3B show that NT3 treatment markedly decreased the percentage of days without stool in both constipated patients and healthy volunteers. In about 48% of days, constipated patients had no stool. After treatment with NT-3, however, constipated patients had no stool in only about 10% of the days (FIG. 3A). Comparing with healthy volunteers who had no stool in about 15% of the days (FIG. 3 B), NT-3 treated constipated patients had fewer days without stool. Healthy volunteers had stool everyday (FIG. 3B).

Figure 4:
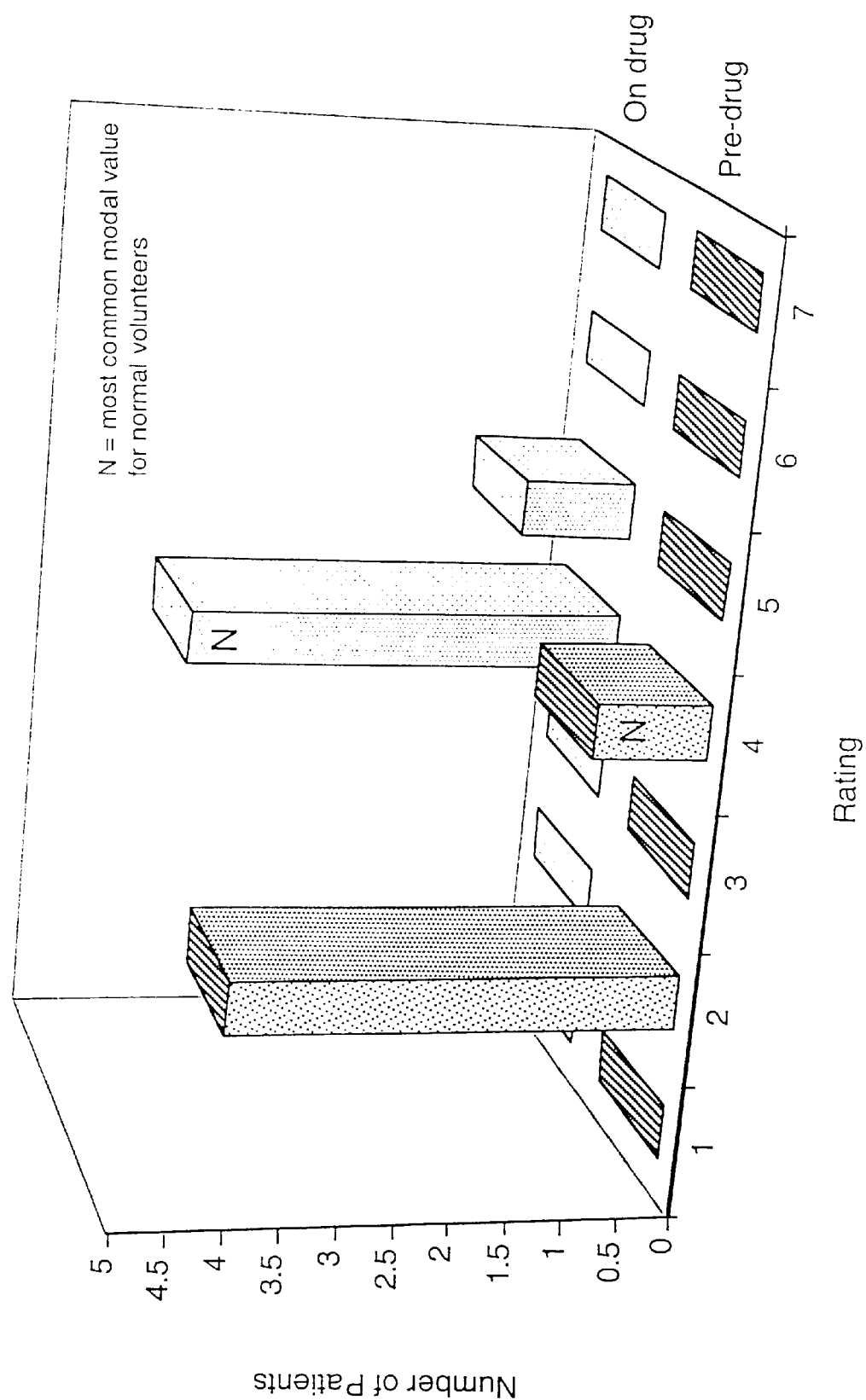
FIG. 4 shows modal ease of passage rating after NT-3 administration.

FIG. 4 shows that r-met HuNT-3 increased most common modal ease of passage 5 rating in constipated patients from 2 to 4, which is the same as that for normal volunteers. The modal use of passage is the most common score assigned to the passage of stools by the patients, using a scale on which a score of 1 indicates the need for manual disempaction or enema and 7 indicates fecal incontinence.

Figure 6A:
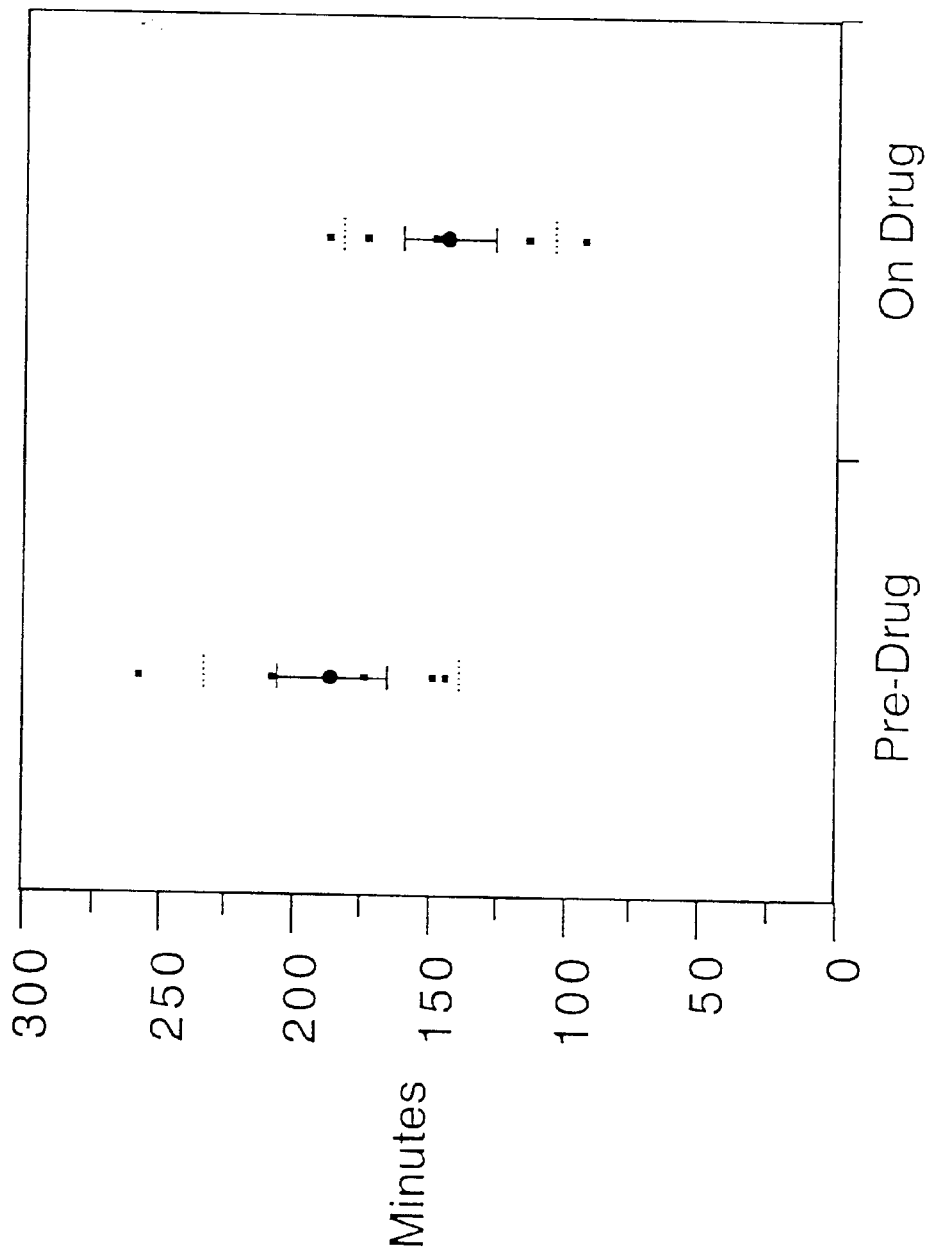
FIGS. 6A and 6B show small bowel transit time by period as affected by NT-3 administration.
Figure 6B:
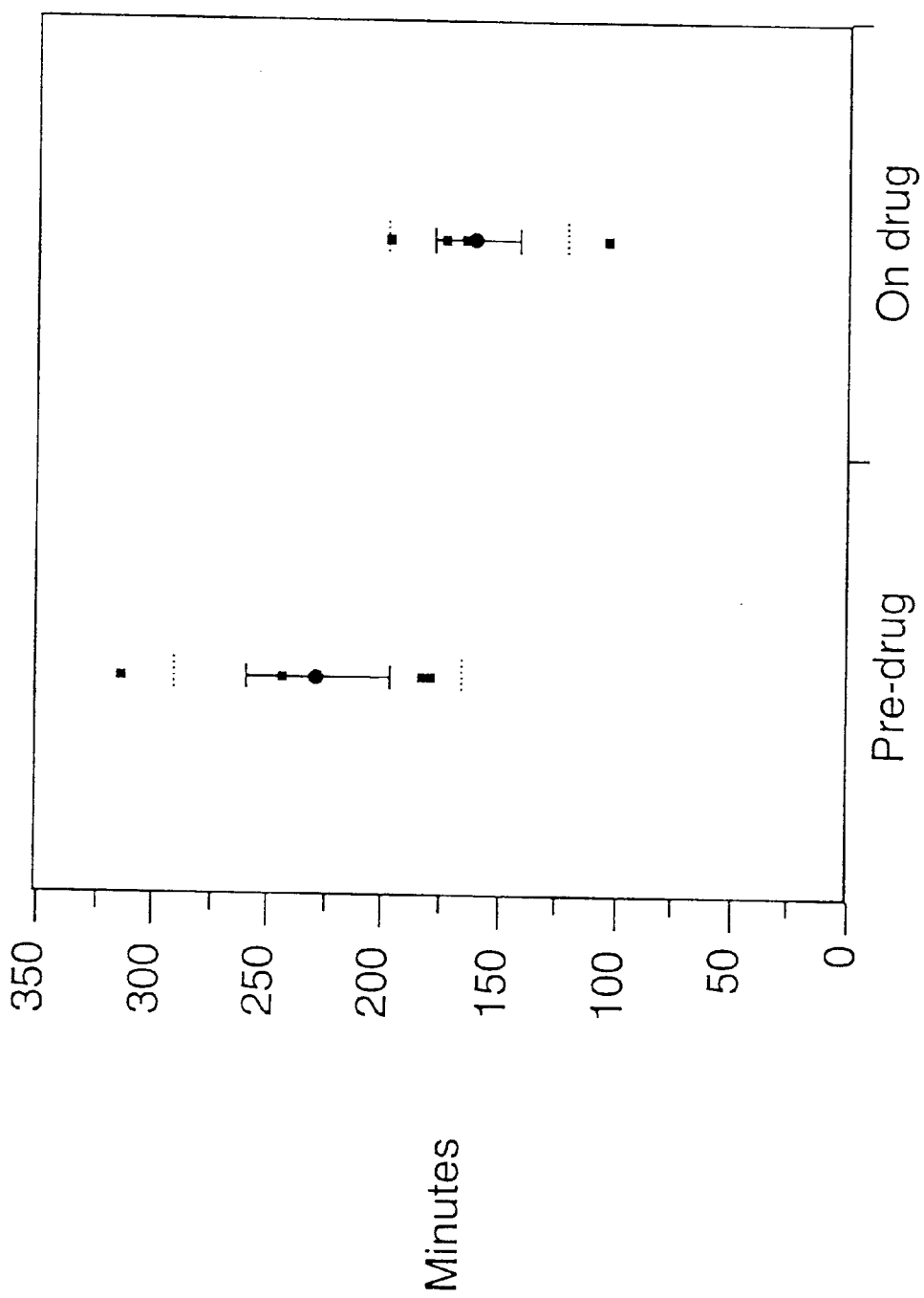

Increased gastrointestinal motility. FIGS. 5A and 5B show that NT-3 treatment shortened gastric emptying half time in both healthy and constipated patients. FIG. 6A (constipated patients) and 6B (normal volunteer) show that small bowel transit time was decreased by NT-3 treatment. FIGS. 7A–7D show that NT-3 increased colonic motility as reflected by the geometric center of the fecal bolus (FIG. 7A shows the advancement of geometric center of fecal bolus at 24 hours (GC24) in constipated patients; FIG. 7B shows the advancement geometric center of decal bolus at 48 hours (GC48) in constipated patients; FIG. 7C shows advancement of GC24 in normal volunteers; FIG. 7D shows advancement of GC48 in normal volunteers).

Table 1 is a summary and statistical analysis of the clinical trial with six constipated patients. Overall, NT-3 accelerated gastric emptying and orocecal transit (as measured by colonic filling at 6 hours) in patients with constipation. It also accelerated orocecal and clonic transit in health volunteers.

TABLE 1

|  | pre-NT-3 | post-NT-3 |
|---|---|---|
| Gastric emptying at 2 h | 48 ± 8 | 63 ± 4* |
| Small bowel transit time, min | 194 ± 19 | 138 ± 16 |
| Colonic filling at 6 h (%) | 50 ± 14 | 87 ± 7* |
| Geometric center at 24 h | 2.4 ± 0.3 | 3.6 ± 0.6* |
| Geometric center at 48 h | 3.5 ± 0.5 | 4.4 ± 0.4* |
| Proximate colonic emptying, $PCEt_{1/2}$, | 3.2 ± 6 | 2.6 ± 6 |

*$P < 0.05$ vs pre-NT-3

Safety of NT-3 treatment. During the treatment period, none of the healthy volunteers or constipated patients showed serious or life threatening adverse events. One patient with a questionable cardiac history and a slow resting pulse at baseline developed prolonged, reversible sinus bradycardia. Another patient developed excessive increase in stool frequency. Observed adverse events are summarized in Table 2.

TABLE 2

|  | Constipated N = 5 | | Normals N = 4 | | Combined N = 9 | |
|---|---|---|---|---|---|---|
| Events | N | % | N | % | N | % |
| ABDOMINAL PAIN | 0 | 0% | 2 | 50% | 2 | 22% |
| ASTHENIA | 1 | 20% | 2 | 50% | 3 | 33% |
| BRADYCARDIA | 1 | 20% | 0 | 0% | 1 | 11% |
| DIARRHEA | 0 | 0% | 1 | 25% | 1 | 11% |
| DIZZINESS | 1 | 20% | 0 | 0% | 1 | 11% |
| ECCHYMOSIS | 0 | 0% | 1 | 25% | 1 | 11% |

TABLE 2-continued

|  | Constipated N = 5 | | Normals N = 4 | | Combined N = 9 | |
| --- | --- | --- | --- | --- | --- | --- |
| Events | N | % | N | % | N | % |
| EMOTIONAL LABILITY | 1 | 20% | 0 | 0% | 1 | 11% |
| FEVER | 0 | 0% | 1 | 25% | 1 | 11% |
| FLATULENCE | 1 | 20% | 1 | 25% | 2 | 22% |
| HYPERESTHESIA | 1 | 20% | 0 | 0% | 1 | 11% |
| INCREASED APPETITE | 0 | 0% | 1 | 25% | 1 | 11% |
| INJECTION SITE REACTION | 1 | 20% | 1 | 25% | 2 | 22% |
| PAIN | 1 | 20% | 1 | 25% | 2 | 22% |
| PARESTHESIA | 1 | 20% | 1 | 25% | 2 | 22% |
| PERIPHERAL EDEMA | 0 | 0% | 1 | 25% | 1 | 11% |
| TASTE PERVERSION | 1 | 20% | 0 | 0% | 1 | 11% |
| ULCERATIVE STOMATITIS | 1 | 20% | 0 | 0% | 1 | 11% |
| URINARY TRACT INFECTION | 1 | 20% | 0 | 0% | 1 | 11% |
| VASODILATATION | 1 | 20% | 0 | 0% | 1 | 11% |
| VOMITING | 0 | 0% | 1 | 25% | 1 | 11% |

Figure 8:
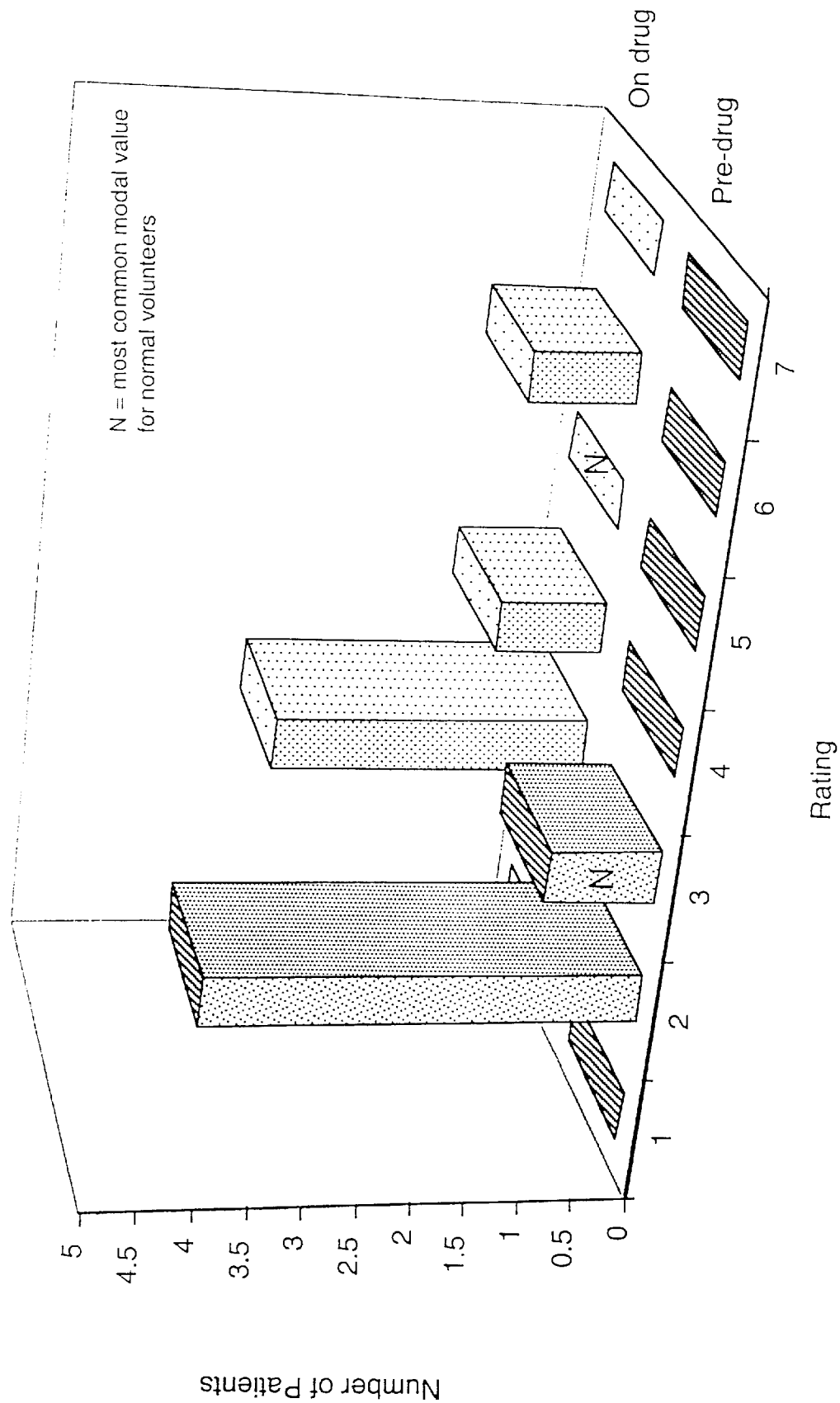
FIG. 8 shows modal stool form in constipated patients.
Figure 9:
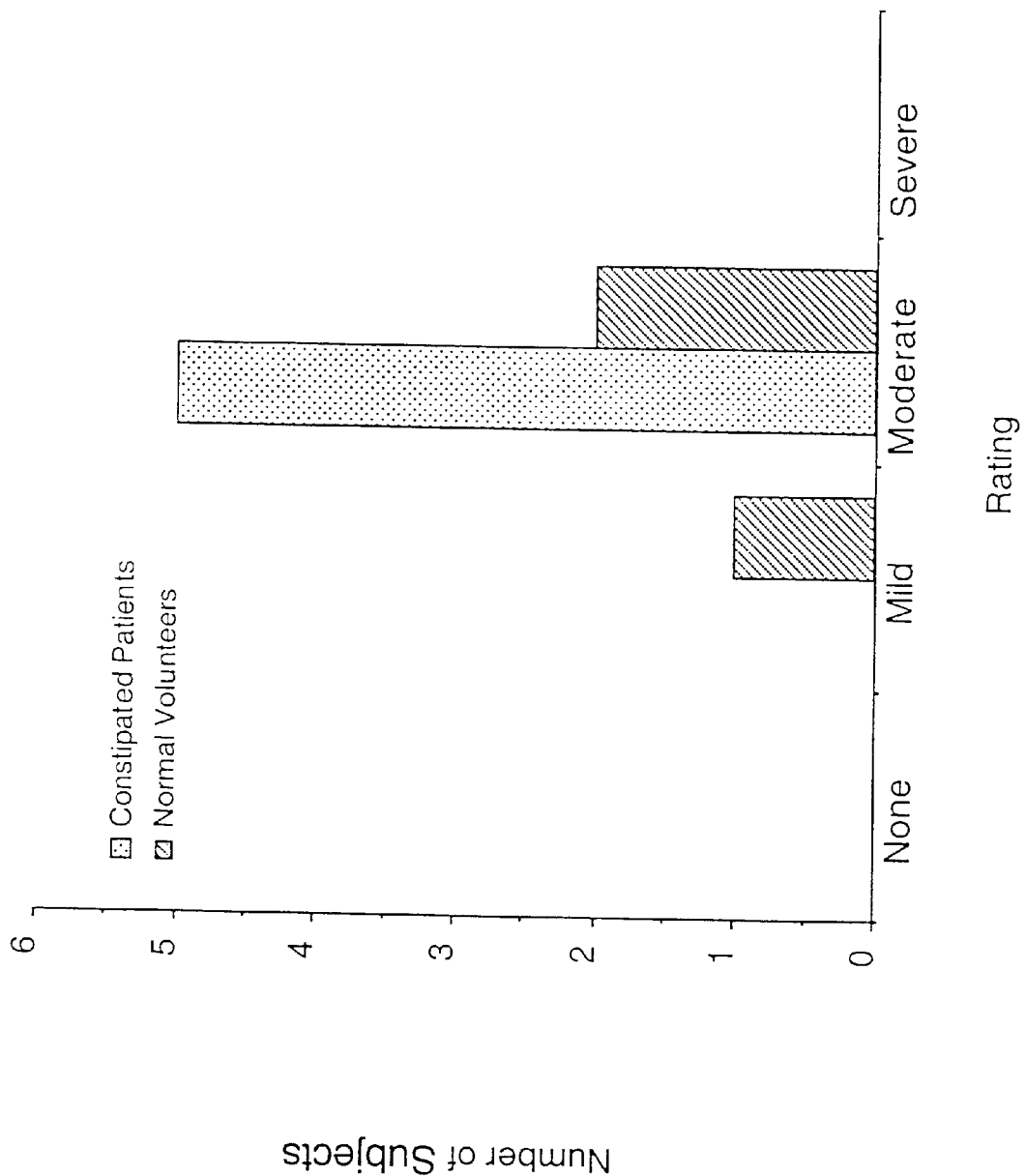
FIG. 9 shows subject's assessment of softening of stool form after NT-3 administration.

While NT-3 treatment increased the frequency of stool and enhanced ease of passage, the treatment did not cause severe softening of stool that would have been characterized as "diarrhea." FIG. 8 shows that most constipated patients reported stool rating softer, using a scale on which 1 is pellets and 7 is watery diarrhea, than that of normal volunteers. Most of the NT-3 treated subjects (both constipated patients and normal volunteers) reported moderate stool form (FIG. 9).

Figures 10A, 10B:
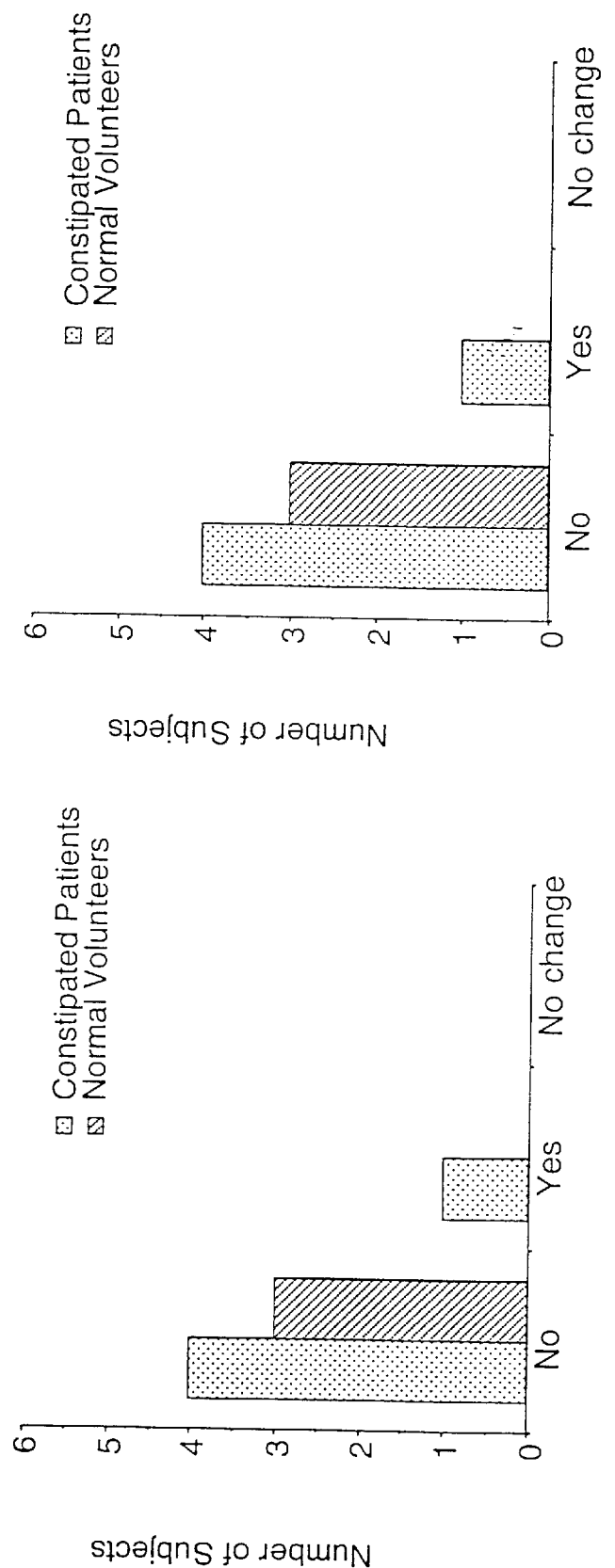
FIGS. 10A and 10B show that changes in bowel function are not characterized as diarrhea subjectively and objectively.

Except for one subject, the changes in bowel function were not characterized as "diarrhea" (FIGS. 10A and 10B). With respect to whether a change in bowel function would be characterized as diarrhea, FIG. 10A shows the answers of subjects, whereas FIG. 10B shows the results of the investigator's evaluation. The changes in gastrointestinal function in eight out of the nine subjects were not characterized as an adverse event if the clinical trial was conducted for an indication other than constipation.

Figure 11:
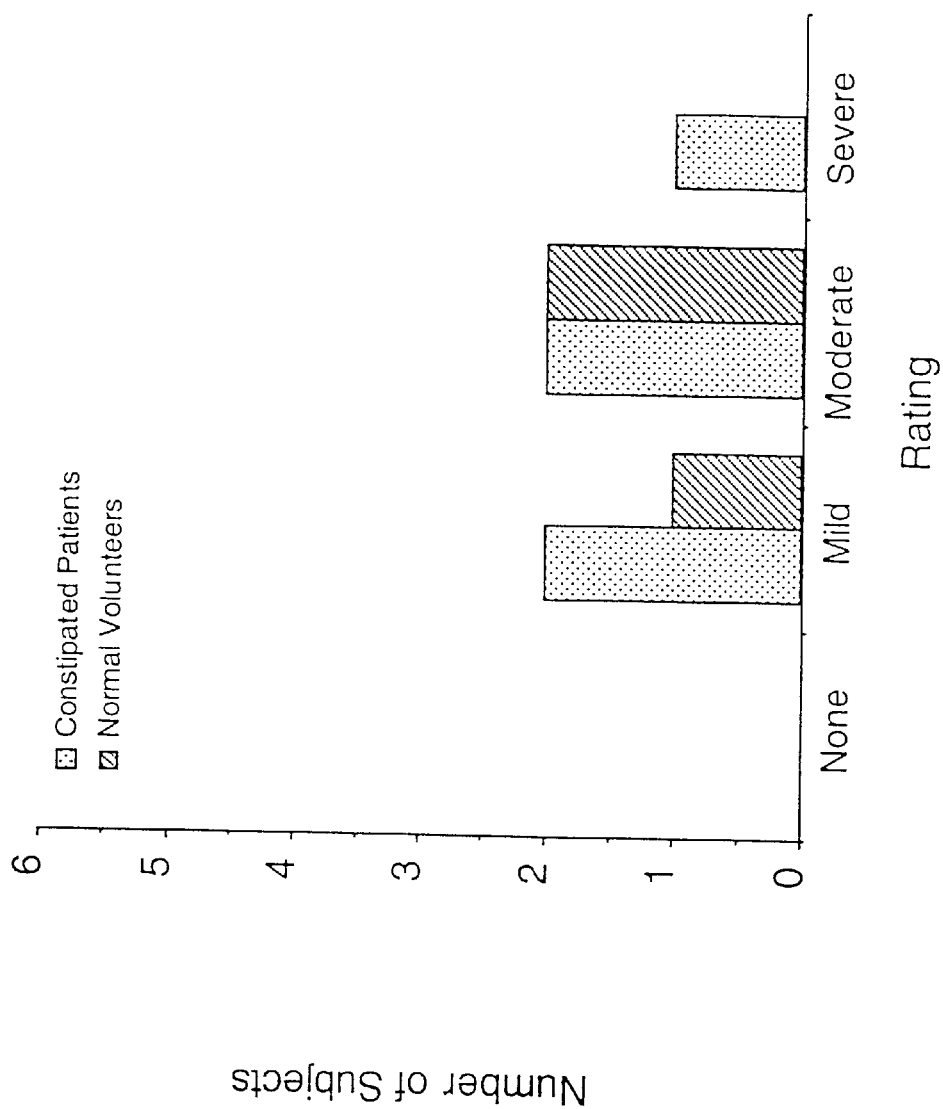
FIG. 11 shows subject's assessment of increase in stool frequency after NT-3 administration.
Figure 12:
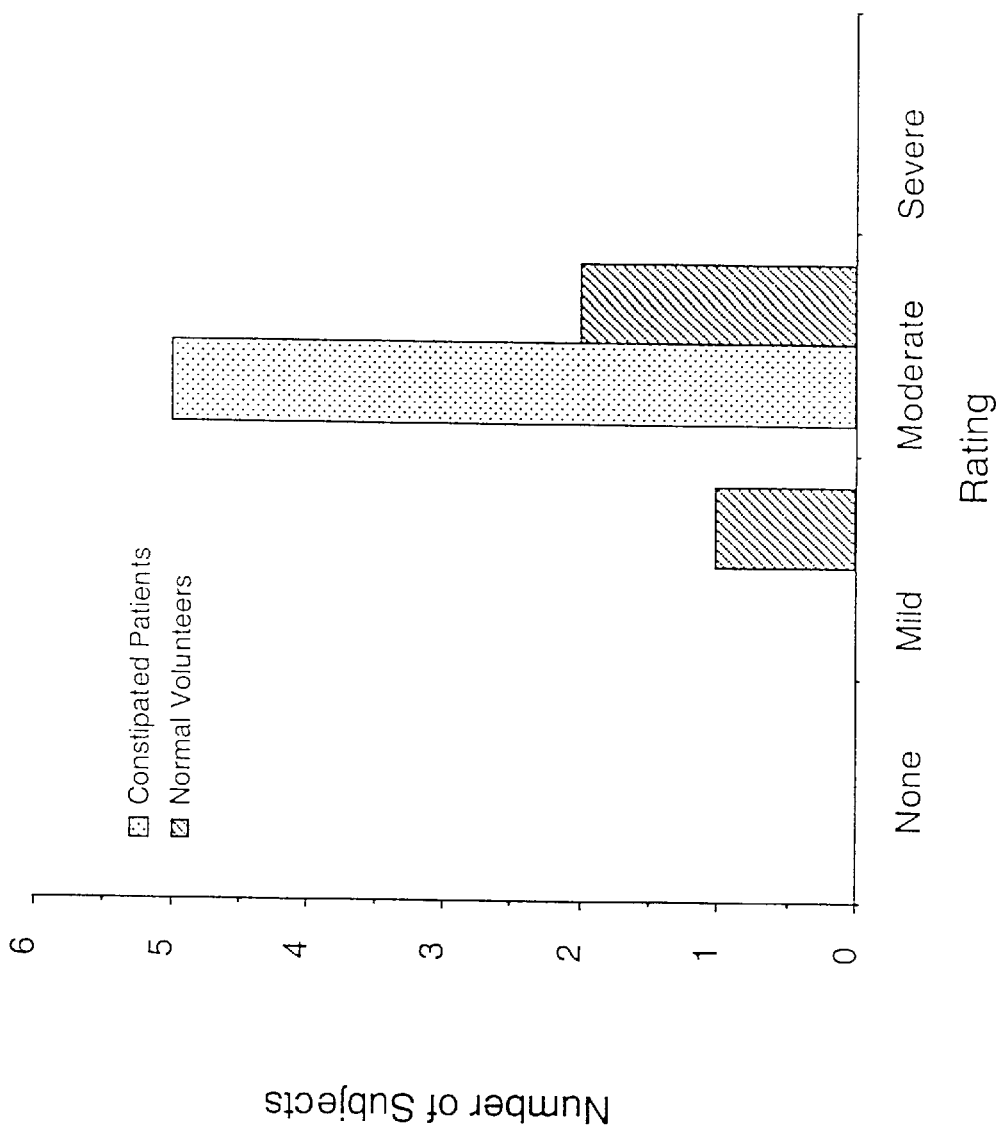
FIG. 12 shows subject's assessment of increase in ease of passage after NT-3 administration.
Figure 13:
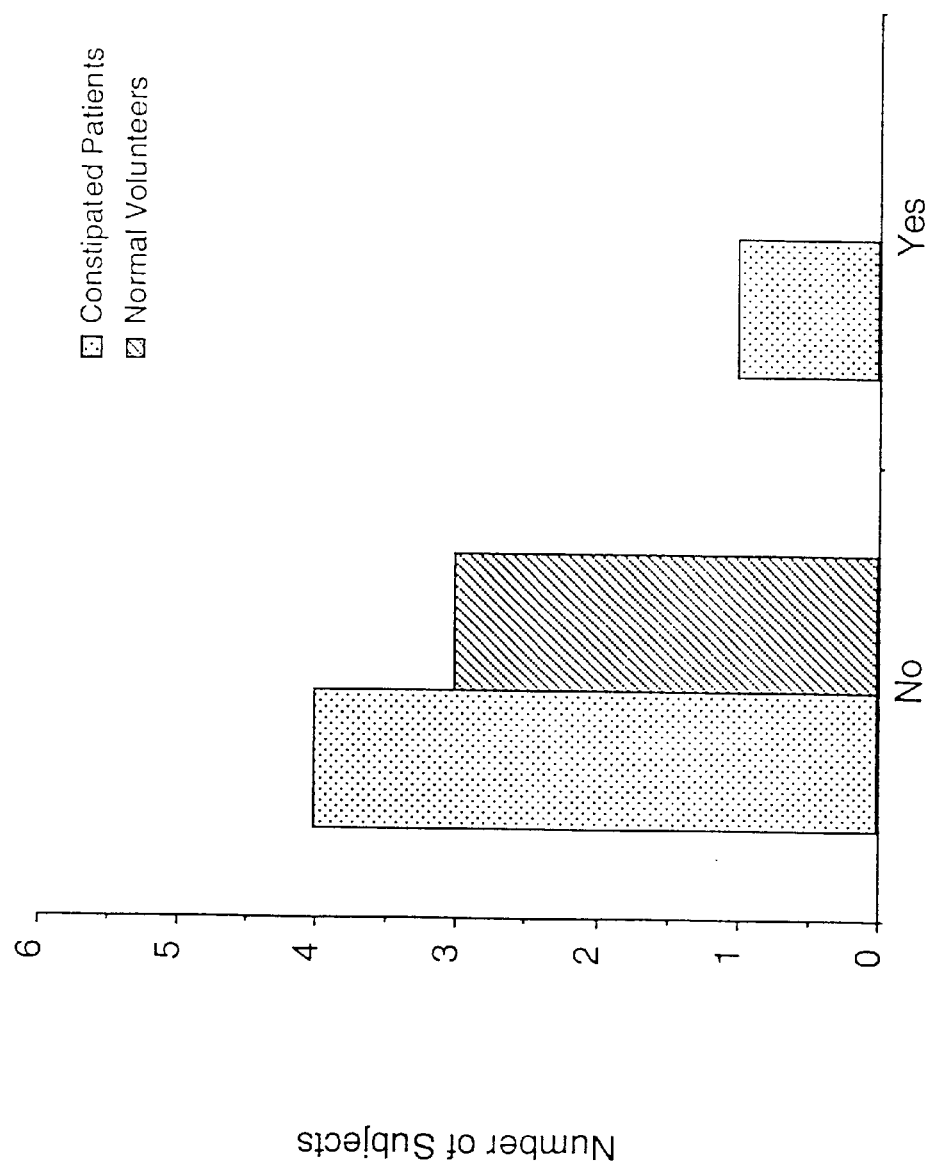
FIG. 13 shows changes in gastrointestinal function after NT-3 administration that would be regarded as an adverse event in a trial for another indication.

Most subjects considered the increase in stool frequency during administration of NT-3 as moderate or mild (FIG. 11, data from five constipated patients and three normal volunteers). Only one normal volunteer considered the increase as severe (FIG. 11). Similarly, none of the subjects considered the increase in ease of passage during administration of NT-3 as severe (FIG. 12, data from five constipated patients and three normal volunteers). Most subjects rated the increase as moderate (FIG. 12). Change in gastrointestinal function in majority of the subjects (four constipated patients and three normal volunteers) would not have been reported as an adverse event if the trial were for another indication (FIG. 13).

In conclusion, subcutaneous injection of a recombinant NT-3 is a safe and effective means for enhancing gastrointestinal motility and relieving constipation.

The present invention is not to be limited in scope by the exemplified embodiments which are intended as illustrations of single aspects of the invention and any sequences which are functionally equivalent are within the scope of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A method of treating or ameliorating a gastrointestinal hypomotility disorder comprising administering to a subject in need of such treatment a composition consisting essentially of a therapeutically effective amount of a neurotrophin-3 receptor activating compound such that the disorder is treated or ameliorated.

2. The method of claim 1 wherein said subject is a human patient.

3. The method of claim 1 wherein said neurotrophin receptor is trkC receptor.

4. The method of claim 1 wherein said compound is a neurotrophin-3.

5. The method of claim 4 wherein said neurotrophin-3 is a recombinant neurotrophin-3.

6. The method of claim 5 wherein said recombinant neurotrophin-3 is a recombinant methionyl human neurotrophin-3.

7. The method of claim 6 wherein said effective amount is in the range of 25–500 µg of said recombinant methionyl neurotrophin-3 per kg of body weight of said subject.

8. The method of claim 7 wherein said effective amount is in the range of 100–300 µg of said recombinant methionyl neurotrophin-3 per kg of body weight of said subject.

9. The method of claim 8 wherein said administering is performed subcutaneously.

10. The method of claim 9 wherein said administering is performed using a subcutaneously implanted sustained release device.

11. The method of claim 8 wherein said administering is performed orally.

12. The method of claim 8 wherein said administering is performed by subcutaneous, intravenous, intramuscular, intrathecal or intraperitoneal injection.

13. The method of claim 8 wherein said administering is performed transdermally.

14. The method of claim 1 wherein said compound is a neurotrophin-3 analogue.

15. The method of claim 1 wherein said gastrointestinal hypomotility is acute constipation.

16. The method of claim 15 wherein said acute constipation is associated with orthopedic, gynecological, thoracic or urological surgery.

17. The method of claim 15 wherein said acute constipation occurs in a coronary care unit or an intensive care unit.

18. The method of claim 1 wherein said gastrointestinal hypomotility is chronic constipation.

19. The method of claim 18 wherein said chronic constipation is associated with enteric neuropathy, Parkinson's disease, multiple sclerosis, chronic use of opiate pain killers, irritable bowel syndrome, or constipation in hospitalized patients.

20. The method of claim 19 wherein said chronic constipation is associated with spinal cord injury.

21. The method of claim 20 wherein said chronic constipation is associated with paraplegia.

22. The method of claim 20 wherein said chronic constipation is associated with quadriplegia.

23. A method of treating or ameliorating a gastrointestinal hypomotility disorder comprising administering to a subject in need of such treatment a composition consisting essentially of a therapeutically effective amount of a neurotrophin-3 receptor activating compound such that the disorder is treated or ameliorated, and wherein the disorder is caused by or associated with a pathological condition selected from the group consisting of obstipation, idiopathic abdominal distention, irritable bowel syndrome, megacolon associated with hypothyroidism, pseudo-obstruction of the gastrointestinal tract, hypomotility of the stomach and colon associated with diabetes mellitus, myopathic disorders, geriatric hypomotility disorders, jejunal-ileal bypass with secondary megacolon, hypomotility associated with cancer chemotherapy, hypomotility associated with severe burns, hypomotility associated with syndromes of depression, post-operative intestinal distension, and use of opiate pain killers.

24. A method of treating or ameliorating a gastrointestinal hypomotility disorder comprising administering to a subject in need of such treatment a composition consisting essentially of a therapeutically effective amount of a recombinant methionyl neurotrophin-3 such that the disorder is treated or ameliorated, and wherein the effective amount is in the range of 25–500 µg/kg body weight of said subject.

25. The method of claim 24 wherein said effective amount is in the range of 100–300 µg/kg body weight of said subject.

26. A method of treating or ameliorating a gastrointestinal hypomotility disorder comprising administering to a subject in need of such treatment a composition consisting essentially of a therapeutically effective amount of a neurotrophin-3 receptor activating compound such that the disorder is treated or ameliorated, and wherein the disorder is of unknown cause.

27. A method of treating or ameliorating a gastrointestinal hypomotility disorder comprising administering to a healthy subject in need of such treatment a composition consisting essentially of a therapeutically effective amount of a neurotrophin-3 receptor activating compound such that the disorder is treated or ameliorated.

28. The method of claim 1, 23, 24, 26 or 27 wherein the composition optionally contains a pharmaceutically acceptable carrier.

* * * * *